US011342069B2

(12) United States Patent
Iantorno et al.

(10) Patent No.: US 11,342,069 B2
(45) Date of Patent: May 24, 2022

(54) APPARATUS AND METHODS FOR STORING AND DISPENSING MEDICATIONS

(71) Applicant: Pat Iantorno, Austin, TX (US)

(72) Inventors: Pat Iantorno, Austin, TX (US); Max Iantorno, Solana Beach, CA (US); Jeff D'Ambrogia, Petaluma, CA (US); Stefan Kanetis, Del Mar, CA (US); Kent Vander Velden, Johnston, IA (US); Tomas Savigliano, San Francisco, CA (US); Samuel Neuendorf, Del Mar, CA (US); Joshua Foss, Round Rock, TX (US); Russell Aldridge, Round Rock, TX (US); Isaac Jones, Round Rock, TX (US); Austin Christenson, Round Rock, TX (US); Joshua Bennett, Round Rock, TX (US); Marc Christenson, Round Rock, TX (US)

( * ) Notice: Subject to any disclaimer, the term of this patent is extended or adjusted under 35 U.S.C. 154(b) by 0 days.

(21) Appl. No.: 17/099,504

(22) Filed: Nov. 16, 2020

(65) Prior Publication Data
US 2021/0074416 A1 Mar. 11, 2021

Related U.S. Application Data

(63) Continuation-in-part of application No. 16/248,297, filed on Jan. 15, 2019, now abandoned, which is a
(Continued)

(51) Int. Cl.
G16H 40/20 (2018.01)
G16H 10/60 (2018.01)
(Continued)

(52) U.S. Cl.
CPC ............ *G16H 40/20* (2018.01); *A61J 7/0076* (2013.01); *G06K 7/10861* (2013.01);
(Continued)

(58) Field of Classification Search
CPC ..... G16H 20/13; G16H 40/20; G07F 17/0092
See application file for complete search history.

(56) References Cited

U.S. PATENT DOCUMENTS 3,624,792 A  11/1971 Ernest
4,411,351 A  10/1983 Lowder et al.
(Continued)

FOREIGN PATENT DOCUMENTS

JP  2011194030  10/2011
WO  2014197855 A1  12/2014

Primary Examiner — Timothy R Waggoner
(74) Attorney, Agent, or Firm — Vander Velden Law Firm, LLC; Melinda S. Vander Velden

(57) ABSTRACT

An apparatus for automated storage and dispensing of medications. Medications are stored in one or more inventory storage foam storage plates attached to a frame of the apparatus. Medications are delivered to the apparatus via a locked delivery container. A carrier mechanism retrieves medications from the inventory storage container and delivery container and moves medications to various subsystems of the apparatus. Information related to medications is communicated to a remote pharmacist prior to dispensing the medication. Multiple installations of the apparatus are centrally coordinated.

12 Claims, 18 Drawing Sheets

Related U.S. Application Data continuation-in-part of application No. 15/058,532, filed on Mar. 2, 2016, now Pat. No. 10,181,014.

(60) Provisional application No. 62/127,244, filed on Mar. 2, 2015.

(51) Int. Cl.

| | | |
|---|---|---|
| *G16H 40/40* | (2018.01) | |
| *G06Q 30/06* | (2012.01) | |
| *G16H 40/67* | (2018.01) | |
| *G06K 7/10* | (2006.01) | |
| *G06K 7/14* | (2006.01) | |
| *G06K 19/06* | (2006.01) | |
| *G16H 80/00* | (2018.01) | |
| *G07F 11/62* | (2006.01) | |
| *G06Q 20/18* | (2012.01) | |
| *G06Q 10/08* | (2012.01) | |
| *A61J 7/00* | (2006.01) | |
| *G06K 9/62* | (2022.01) | |
| *G16H 20/13* | (2018.01) | |
| *G07F 17/00* | (2006.01) | |

(52) U.S. Cl.
CPC ......... *G06K 7/1413* (2013.01); *G06K 9/6201* (2013.01); *G06K 19/06028* (2013.01); *G06Q 10/08355* (2013.01); *G06Q 20/18* (2013.01); *G06Q 30/0637* (2013.01); *G07F 11/62* (2013.01); *G07F 17/0092* (2013.01); *G16H 10/60* (2018.01); *G16H 20/13* (2018.01); *G16H 40/40* (2018.01); *G16H 40/67* (2018.01); *G16H 80/00* (2018.01); *A61J 2205/30* (2013.01); *G06K 2007/10504* (2013.01)

(56) References Cited

U.S. PATENT DOCUMENTS

| | | |
|---|---|---|
| 5,468,110 A | 11/1995 | McDonald et al. |
| 5,561,604 A | 10/1996 | Buckley et al. |
| 5,593,267 A | 1/1997 | McDonald et al. |
| 6,152,364 A | 11/2000 | Schoonen et al. |
| 6,230,927 B1 | 5/2001 | Schoonen et al. |
| 6,352,200 B1 | 3/2002 | Schoonen et al. |
| 6,529,801 B1 | 3/2003 | Rosenblum |
| 6,892,941 B2 | 5/2005 | Rosenblum |
| 6,929,149 B2 | 8/2005 | Selfridge et al. |
| 7,063,232 B2 | 6/2006 | Chirnomas |
| 7,152,736 B1 | 12/2006 | Menichini |
| 7,251,546 B2 | 7/2007 | Chirnomas |
| 7,334,701 B2 | 2/2008 | Chirnomas et al. |
| 7,366,586 B2 * | 4/2008 | Kaplan ............... G07F 17/16 700/241 |
| 7,407,064 B2 | 8/2008 | Chirnomas |
| 7,444,203 B2 | 10/2008 | Rosenblum |
| 7,469,820 B2 | 12/2008 | Rosenblum |
| 7,471,993 B2 | 12/2008 | Rosenblum |
| 7,689,318 B2 | 3/2010 | Draper |
| 7,774,097 B2 | 8/2010 | Rosenblum |
| 7,896,243 B2 | 3/2011 | Herskovitz |
| 8,033,424 B2 | 10/2011 | Rosenblum |
| 8,095,236 B2 | 1/2012 | Rudy et al. |
| 8,191,719 B2 | 6/2012 | Ooyen et al. |
| 8,267,310 B2 | 9/2012 | Waugh et al. |
| 8,342,400 B1 * | 1/2013 | Reese ............... G16H 20/13 235/385 |
| 8,465,243 B2 | 6/2013 | Ooyen et al. |
| 8,527,090 B2 | 9/2013 | Monto et al. |
| 8,577,145 B2 | 11/2013 | Panetta |
| 8,647,573 B2 | 2/2014 | Regan et al. |
| 8,695,814 B2 | 4/2014 | Ooyen et al. |
| 8,712,586 B2 | 4/2014 | Allinson |
| 8,738,177 B2 | 5/2014 | Ooyen et al. |
| 8,744,619 B2 | 6/2014 | Rosenblum |
| 8,789,748 B2 | 7/2014 | Waugh et al. |
| 8,849,449 B2 | 9/2014 | Waugh et al. |
| 8,862,266 B2 | 10/2014 | Ooyen et al. |
| 9,036,894 B2 | 5/2015 | Panetta |
| 9,242,794 B2 | 1/2016 | Ooyen et al. |
| 9,495,465 B2 | 11/2016 | Bowers et al. |
| 9,721,418 B2 | 8/2017 | Ooyen et al. |
| 2003/0050731 A1 * | 3/2003 | Rosenblum ......... G07F 17/0092 700/232 |
| 2003/0136794 A1 | 7/2003 | Chirnomas |
| 2003/0234259 A1 | 12/2003 | Selfridge et al. |
| 2004/0026441 A1 | 2/2004 | Chirnomas |
| 2004/0164146 A1 | 8/2004 | Rosenblum |
| 2004/0215369 A1 | 10/2004 | Rosenblum |
| 2005/0192705 A1 * | 9/2005 | Pinney ............... G07F 11/62 700/241 |
| 2005/0211720 A1 | 9/2005 | Chirnomas |
| 2005/0263536 A1 | 12/2005 | Selfridge et al. |
| 2006/0074524 A1 | 4/2006 | Chirnomas |
| 2006/0124656 A1 | 6/2006 | Popovich |
| 2006/0149587 A1 | 7/2006 | Hill et al. |
| 2007/0043469 A1 | 2/2007 | Draper |
| 2007/0162184 A1 | 7/2007 | Pinney et al. |
| 2007/0250346 A1 | 10/2007 | Luciano et al. |
| 2007/0293982 A1 | 12/2007 | Rosenblum |
| 2008/0164279 A1 | 7/2008 | Chirnomas et al. |
| 2008/0272142 A1 | 11/2008 | Chirnomas |
| 2009/0048712 A1 | 2/2009 | Rosenblum |
| 2009/0076650 A1 | 3/2009 | Faes |
| 2009/0144208 A1 | 6/2009 | Blust et al. |
| 2010/0051187 A1 | 3/2010 | Willick et al. |
| 2010/0145506 A1 | 6/2010 | Waugh et al. |
| 2010/0198401 A1 | 8/2010 | Waugh et al. |
| 2010/0232640 A1 | 9/2010 | Friend et al. |
| 2010/0268380 A1 | 10/2010 | Waugh et al. |
| 2010/0324728 A1 | 12/2010 | Rosenblum |
| 2011/0054668 A1 | 3/2011 | Holmes et al. |
| 2011/0229296 A1 | 9/2011 | Ooyen et al. |
| 2011/0231010 A1 | 9/2011 | Panetta et al. |
| 2011/0264259 A1 | 10/2011 | Boyer et al. |
| 2011/0288880 A1 | 11/2011 | Waugh |
| 2012/0004770 A1 | 1/2012 | Ooyen et al. |
| 2012/0012606 A1 | 1/2012 | Longley et al. |
| 2012/0061338 A1 | 3/2012 | Willick et al. |
| 2012/0081225 A1 | 4/2012 | Waugh et al. |
| 2012/0083666 A1 | 4/2012 | Waugh et al. |
| 2012/0089249 A1 | 4/2012 | Rosenblum |
| 2012/0232693 A1 | 9/2012 | Allinson |
| 2012/0310410 A1 * | 12/2012 | Adams ............... A61J 7/0481 700/237 |
| 2013/0204432 A1 | 8/2013 | Panetta et al. |
| 2013/0231775 A1 | 9/2013 | Jefferies et al. |
| 2013/0251479 A1 | 9/2013 | Waugh et al. |
| 2013/0284755 A1 | 10/2013 | Yuyama et al. |
| 2014/0154044 A1 | 6/2014 | Ooyen et al. |
| 2014/0361076 A1 | 12/2014 | Iantorno et al. |
| 2015/0019008 A1 | 1/2015 | Ooyen et al. |
| 2015/0025679 A1 | 1/2015 | Rosenblum |
| 2015/0134106 A1 | 5/2015 | Boyer et al. |
| 2016/0259914 A1 | 9/2016 | Iantorno et al. |
| 2019/0163876 A1 | 5/2019 | Remme et al. |

\* cited by examiner

APPARATUS AND METHODS FOR STORING AND DISPENSING MEDICATIONS

CROSS-REFERENCE TO RELATED APPLICATIONS

This application is a continuation in part of U.S. patent application Ser. No. 16/248,297 filed on Jan. 15, 2019, which claims priority to U.S. patent application Ser. No. 15/058,532 filed on Mar. 2, 2016, which claims priority to U.S. Provisional Patent Application No. 62/127,244 filed on Mar. 2, 2015, the entirety of which are hereby incorporated herein by reference.

FIELD OF THE INVENTION

This invention relates generally to medication dispensers and methods for storing and dispensing medications. In particular, this invention provides a centrally coordinated automated medication dispenser configured to be monitored remotely by a pharmacist who oversees one or more automated medication dispensers, thereby increasing the efficiency of the medication dispensing process. Further efficiencies are achieved by improved logistics, trend observations, and geolocating via a phone application.

BACKGROUND

Traditionally, dispensing of medications has been performed exclusively in a pharmacy setting in which one or more pharmacists must be physically present. Legal requirements in some jurisdictions mandate a certain number of pharmacies per geographical area, resulting in a large number of pharmacies, each of which must be staffed by at least one pharmacist. Because each pharmacist can only serve one pharmacy, a large number of highly trained individuals is needed to staff the many traditional pharmacies in existence, resulting in great expense.

In addition to the expense of supporting traditional pharmacies, a relatively large number of individuals may have unmonitored access to medications stored in traditional pharmacy inventories. This uncontrolled access results in a large number of medications that go missing without the ability to determine precisely who took the medication.

Attempts have been made to remedy the inefficiencies presented by traditional pharmacies with kiosks; however, the medication dispensing kiosks available still rely heavily on pharmacist interaction. In some instances, a pharmacist must restock medications. In other instances, the kiosk functions only to place the pharmacist remotely from the kiosk, and a pharmacist must still instigate and complete the medication dispensing process. The available kiosks also do not address the issue of medication security as medication packages are directly handled by a technician and placed by hand into the kiosk. In addition, the available kiosks do not provide competitive pricing information at a time when the consumer has a choice of where to fill the prescription, and the price of drugs is only shown after approval and only for the drugs being dispensed at that time. For at least these reasons, an apparatus that automatically restocks and dispenses medications with minimal interaction by a pharmacist would be advantageous.

BRIEF SUMMARY

In accordance with one embodiment of the invention, an apparatus for storing and dispensing medications contained in a bottle or other packaging is provided. The apparatus comprises one or more foam storage plates configured to store a number of medication packages within the apparatus. Medications to be stored in inventory storage may be provided in a locked delivery container, and the apparatus is capable of automatically unloading the delivery container to place medications held by the delivery container into inventory storage. Medications are removed from inventory storage or the delivery container by a carrier that is configured to move the medications between various sub-assemblies of the apparatus. A printer assembly is provided to print labels to be adhered on the medication packaging. A computer disposed in the apparatus controls the function of the various other components of the apparatus, communicates with a centralized database that stores patient and medication information and manages inventory. An input device disposed on the apparatus allows technicians, patients, and other users to interact with the apparatus.

Through the use of locked delivery container, the apparatus may be securely restocked by a technician while complying with legal requirements of a jurisdiction. In one embodiment, restocking the apparatus comprises authenticating a technician to access the apparatus. Once the technician is authorized, the apparatus unlocks an access panel, allowing the technician to place the locked delivery container in the apparatus. The apparatus is then locked, and the apparatus automatically unloads the delivery container, identifies the medications that have been placed within it, and places the newly added medications in inventory storage.

Medications may be dispensed to patients with minimal intervention by a pharmacist. A patient refills a prescription by first providing identifying information to the apparatus through an input device such as a touchscreen. The apparatus verifies that the patient has a valid prescription for the requested medication through communication with the centralized database. The apparatus also determines if the apparatus contains the medication the patient has requested. The medication is picked from its location in inventory storage, labelled, scanned by a barcode reader, and an image is captured. The patient's prescription and images of the medication before and after labelling are communicated to a pharmacist, who inspects the information communicated from the apparatus to the pharmacist and may approve or reject dispensing the medication to the patient based on the inspection. This embodiment of a dispensing process is advantageous because it minimizes the pharmacist's interaction, yet satisfies the legal requirements of many jurisdictions.

Lock boxes located externally to the apparatus may be used to store dispensed medications, extending the capacity of inventory storage. Access to the lock boxes is controlled by the apparatus, and a technician may move the medications into the lock boxes.

Software running on a phone or similar device may be used to find the nearest apparatus containing all medications required by the user.

Required inventory may be predicted based on trends observed in dispensing history. Patients may receive medications at the site of the apparatus or may choose other options for receiving their medications including placing a mail order for medications, having medications delivered, or transferring medications to a pharmacy. Competitive pricing information may be provided by the apparatus, allowing patients to choose how and where they would like to receive their medications.

While the embodiments described refer to medications, other items may be similarly stored and dispensed from the described apparatus.

BRIEF DESCRIPTION OF THE DRAWINGS

Figure 1:
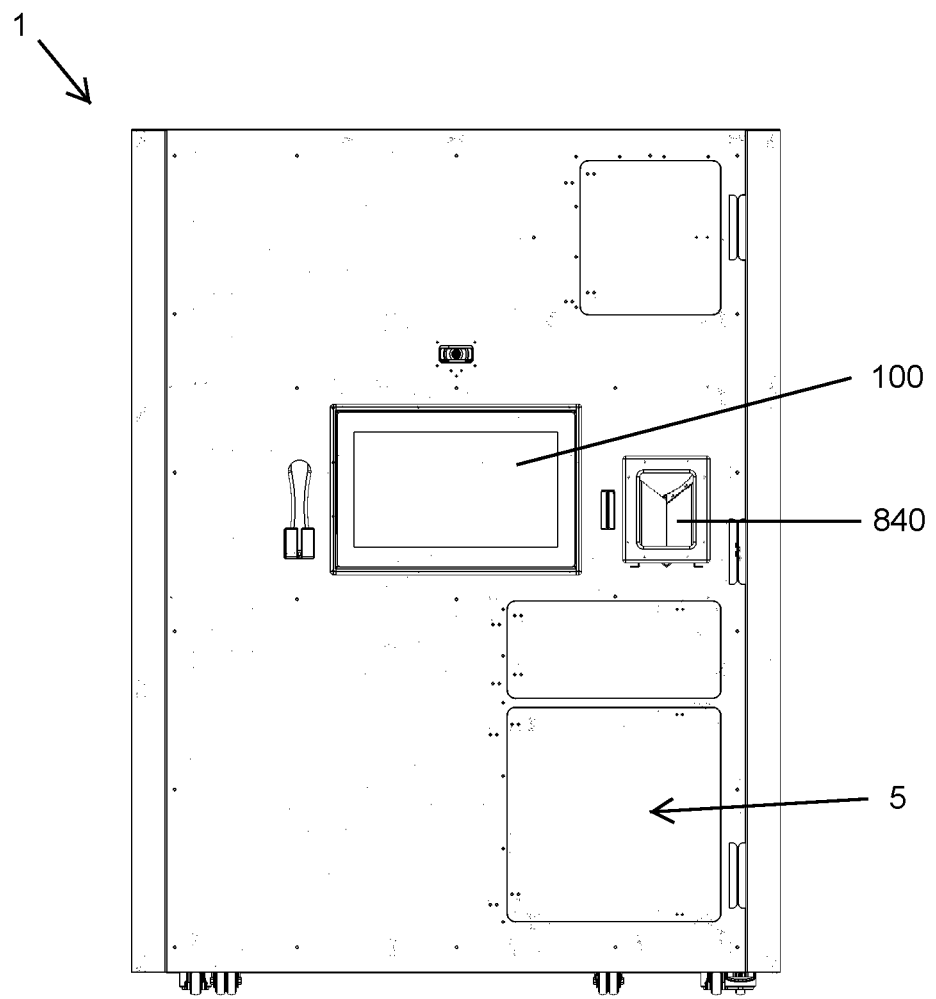

Having thus described the invention in general terms, reference will now be made to the accompanying drawings, which are not necessarily drawn to scale, and wherein:

FIG. 1 illustrates a front external view of an apparatus for storing and dispensing items such as medications in accordance with an embodiment of the invention.

Figure 2:
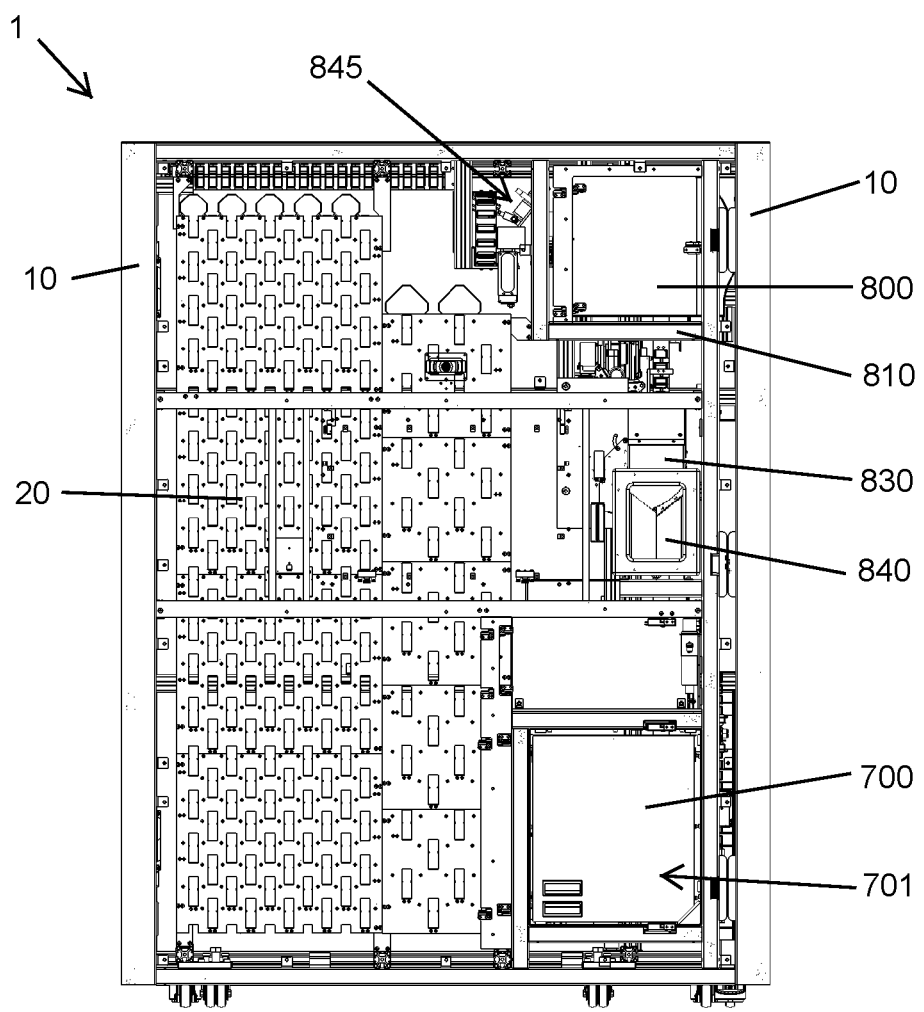

FIG. 2 illustrates a front view of the internal structure of an apparatus for storing and dispensing items such as medications in accordance with an embodiment of the invention.

Figure 3:
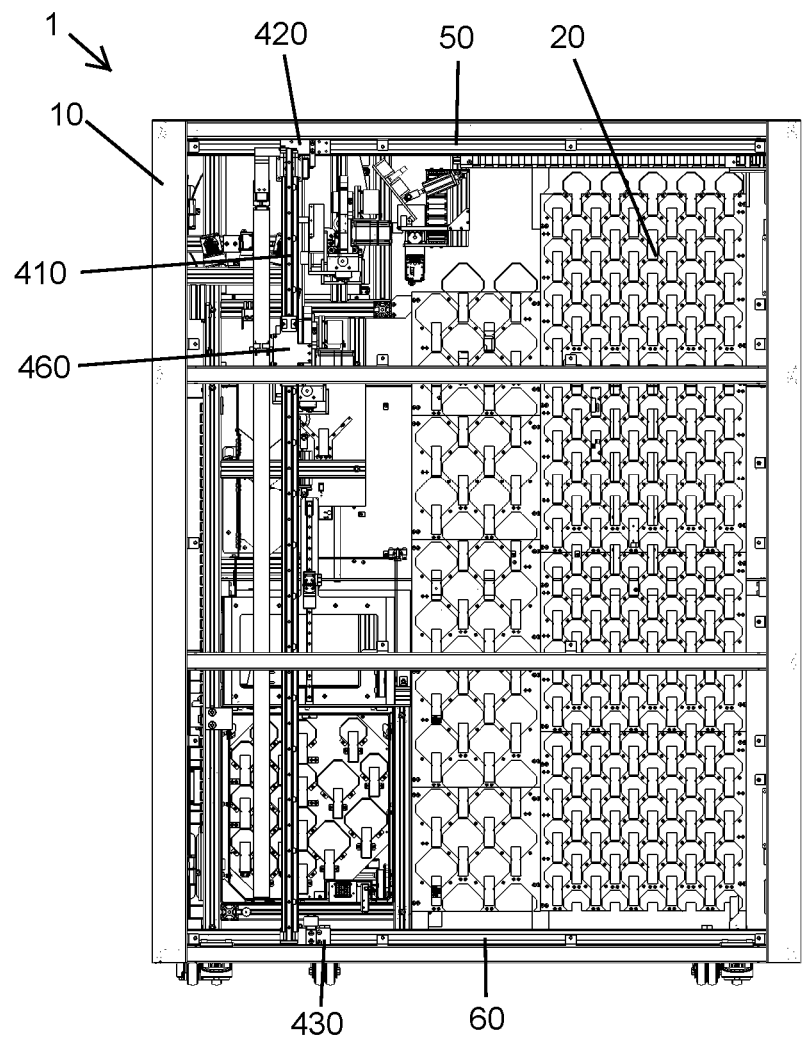

FIG. 3 illustrates a rear view of the internal structure of an apparatus for storing and dispensing items such as medications in accordance with an embodiment of the invention.

Figure 4:
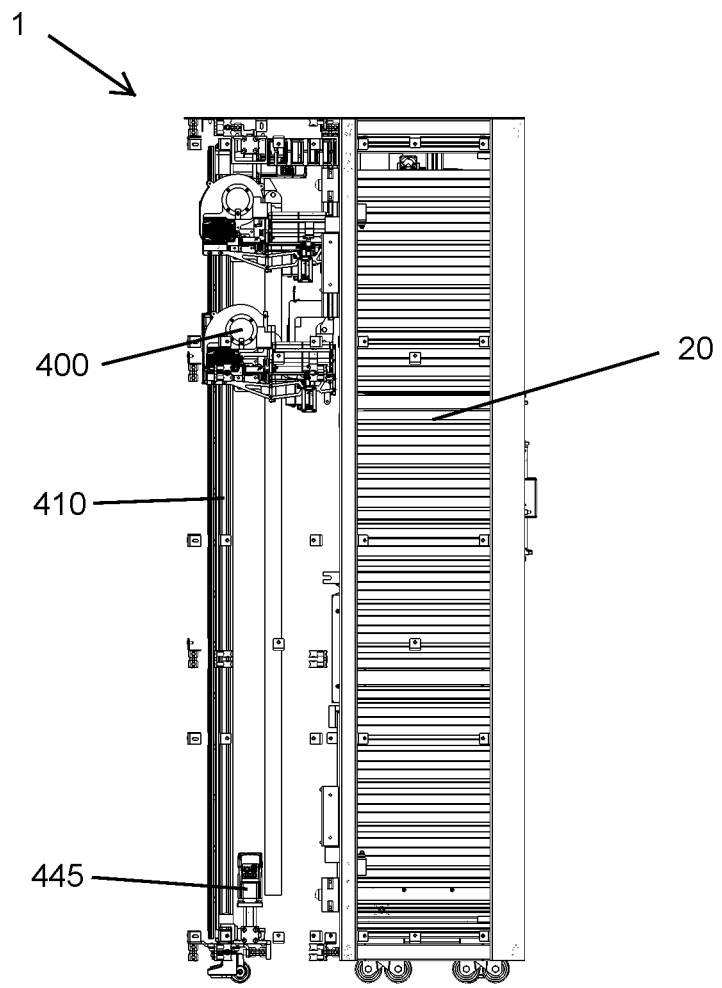

FIG. 4 illustrates a side view of the internal structure of an apparatus for storing and dispensing items such as medications in accordance with an embodiment of the invention.

Figure 5:
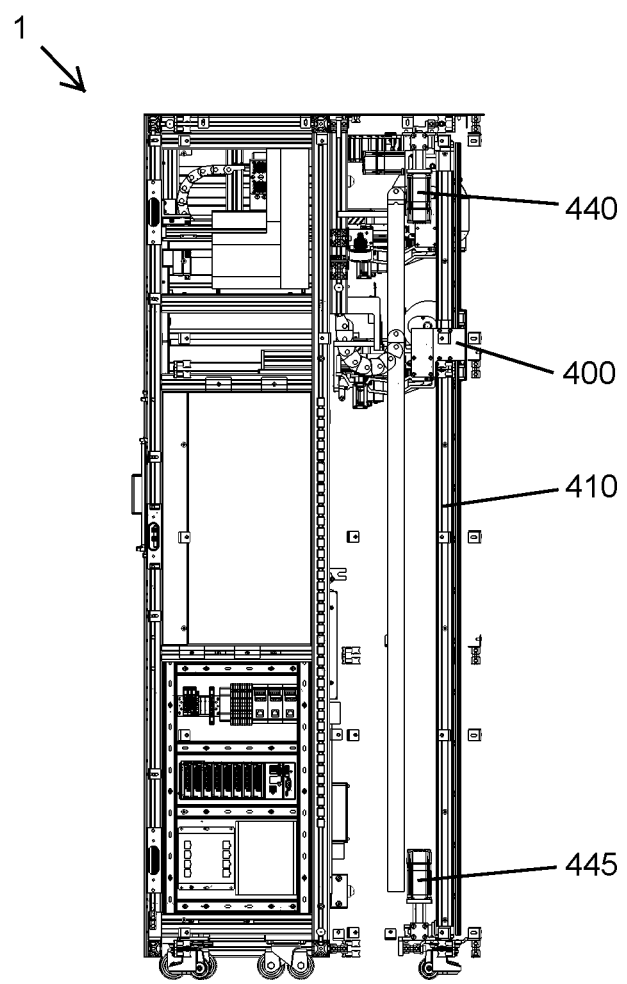

FIG. 5 illustrates a side view of the internal structure of an apparatus for storing and dispensing items such as medications in accordance with an embodiment of the invention.

Figure 6:
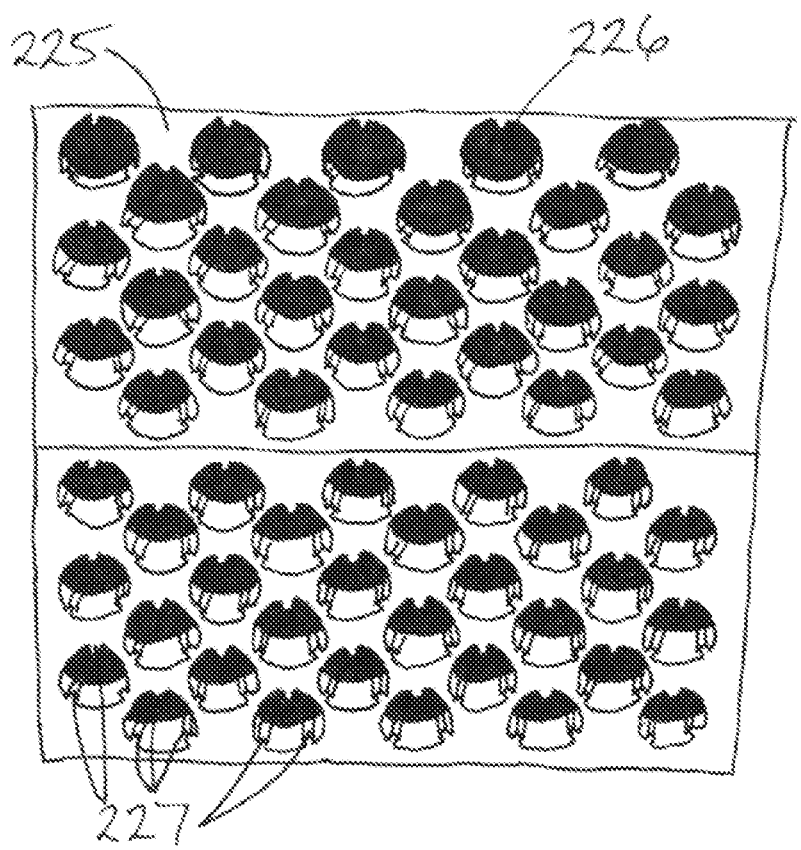

FIG. 6 illustrates a foam storage plate in accordance with an embodiment of the invention.

Figure 7:
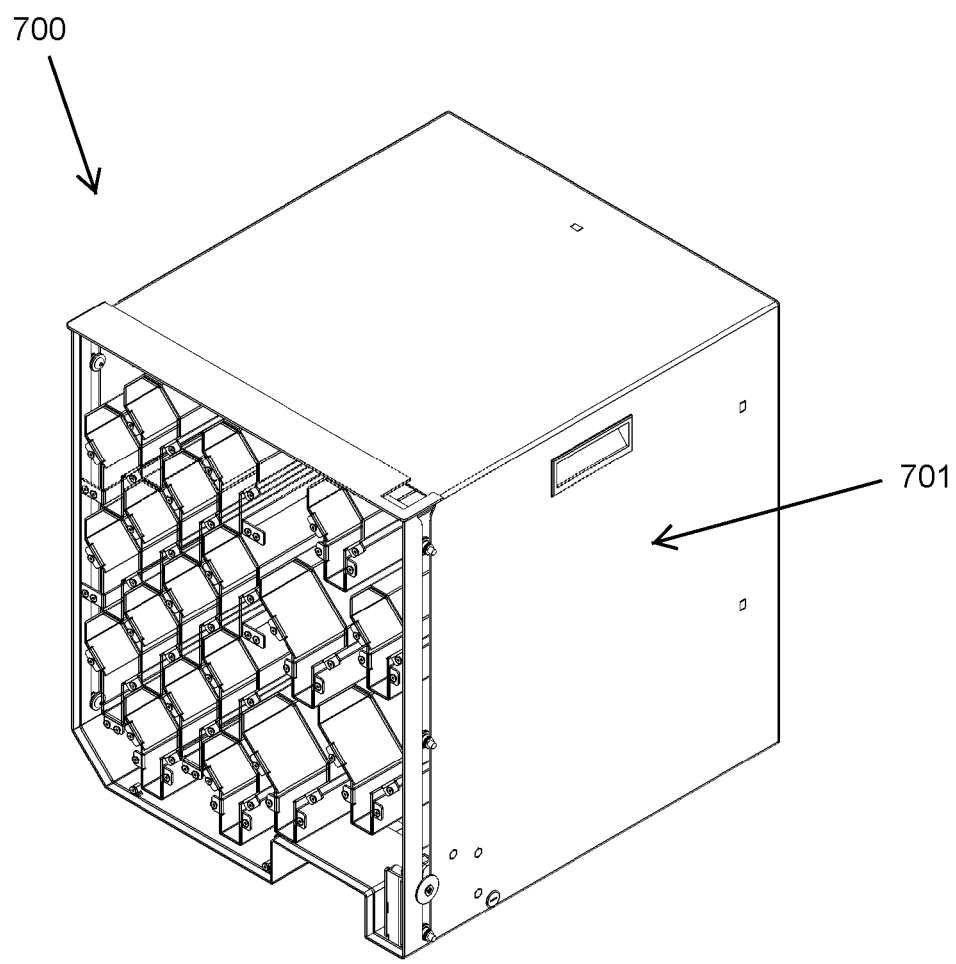

FIG. 7 illustrates a delivery container in accordance with an embodiment of the invention.

Figure 8:
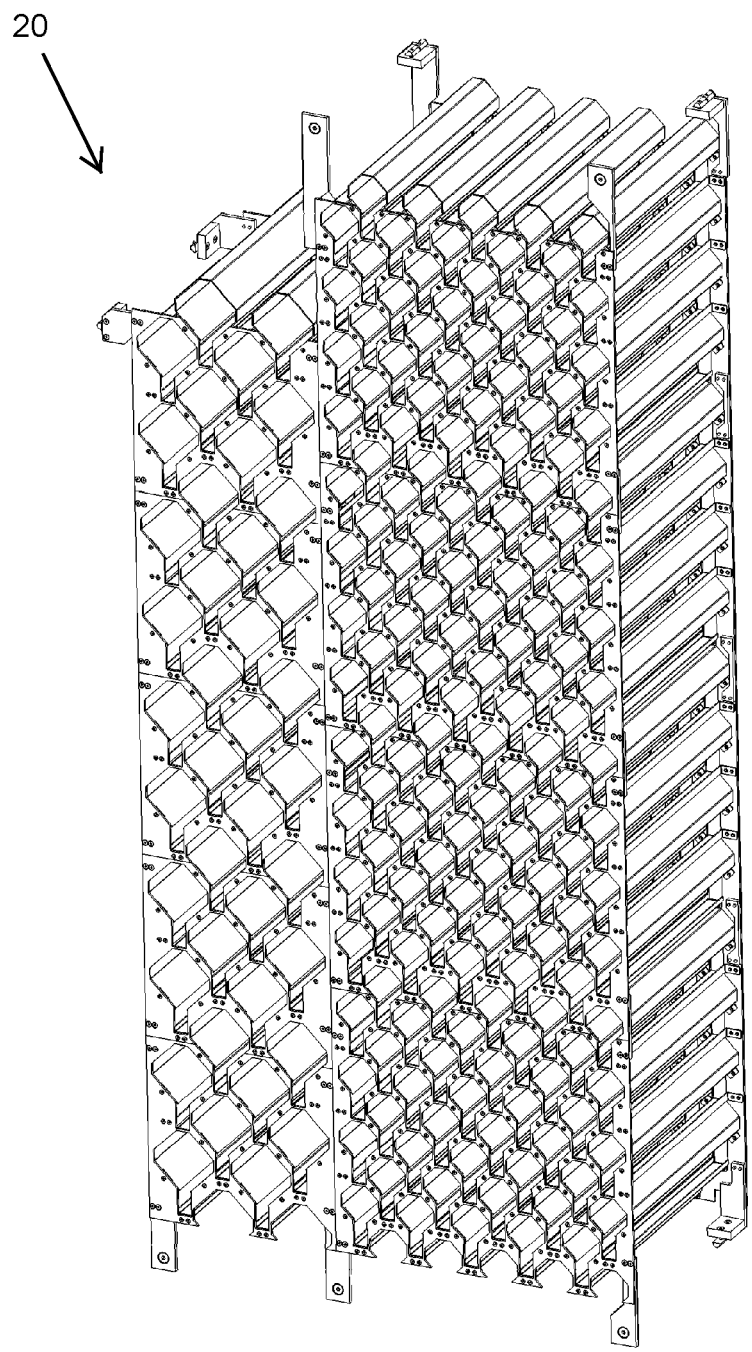

FIG. 8 illustrates an inventory storage container for storing items such as medications in accordance with an embodiment of the invention.

Figure 9:
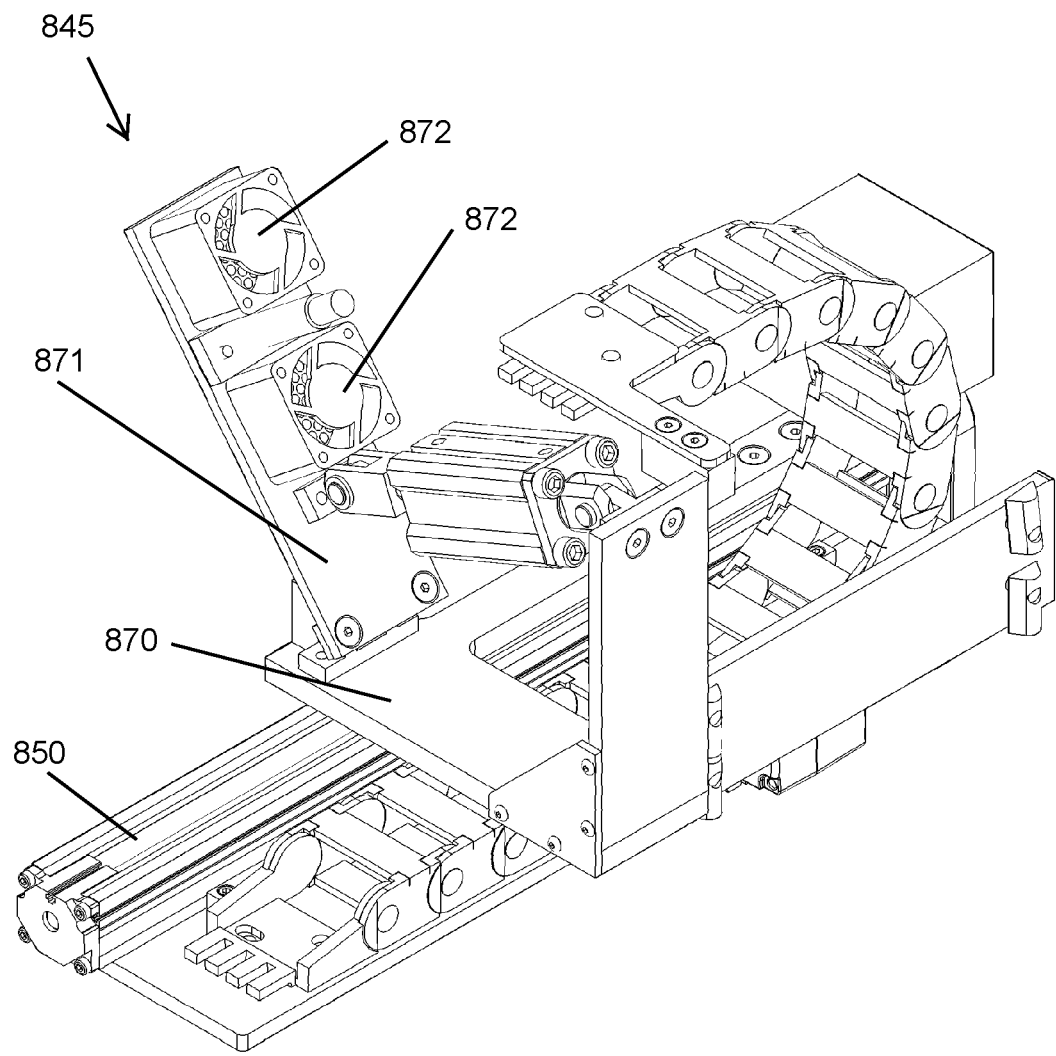

FIG. 9 illustrates a label handling assembly in accordance with an embodiment of the invention.

Figure 10:
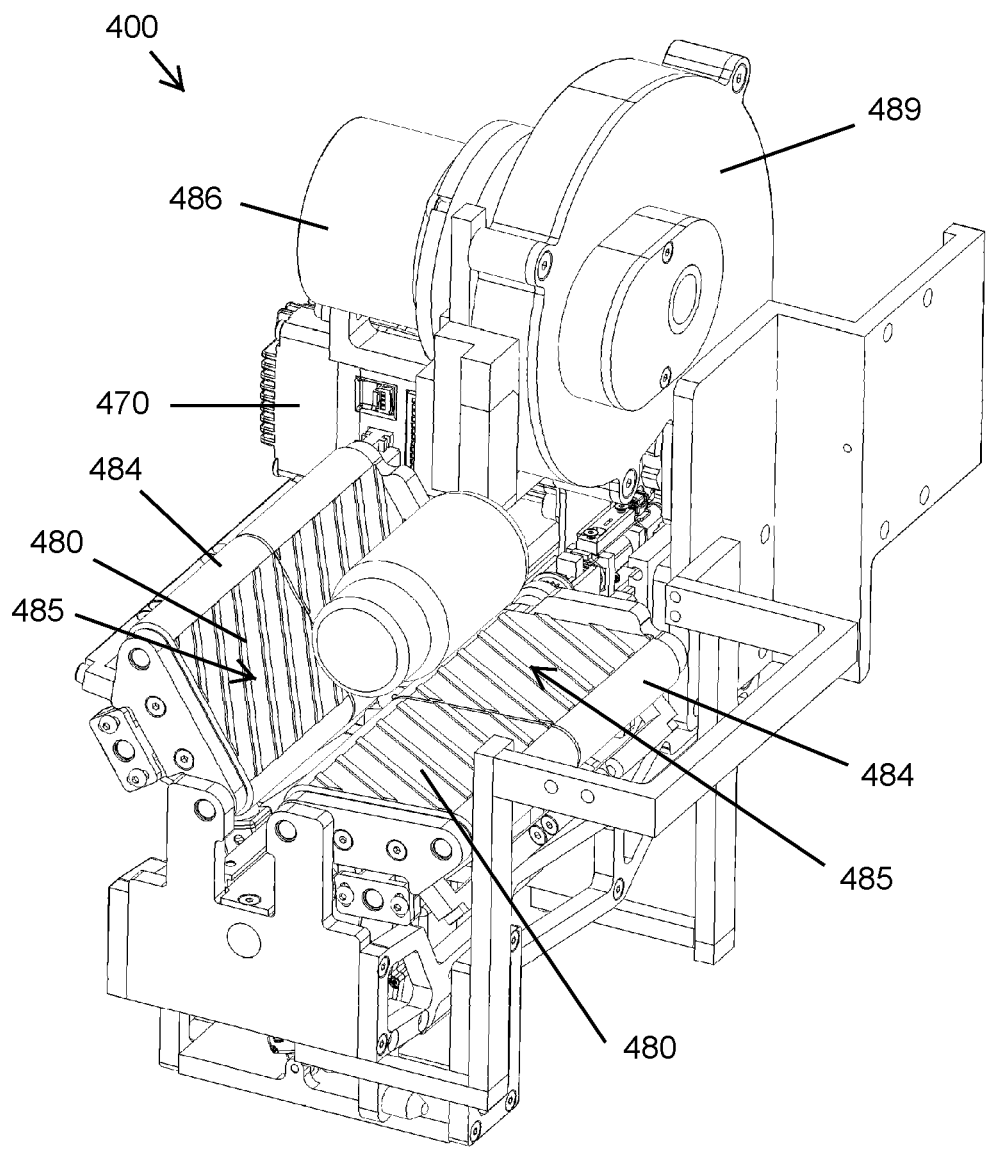

FIG. 10 illustrates a carrier in accordance with an embodiment of the invention.

Figure 11:
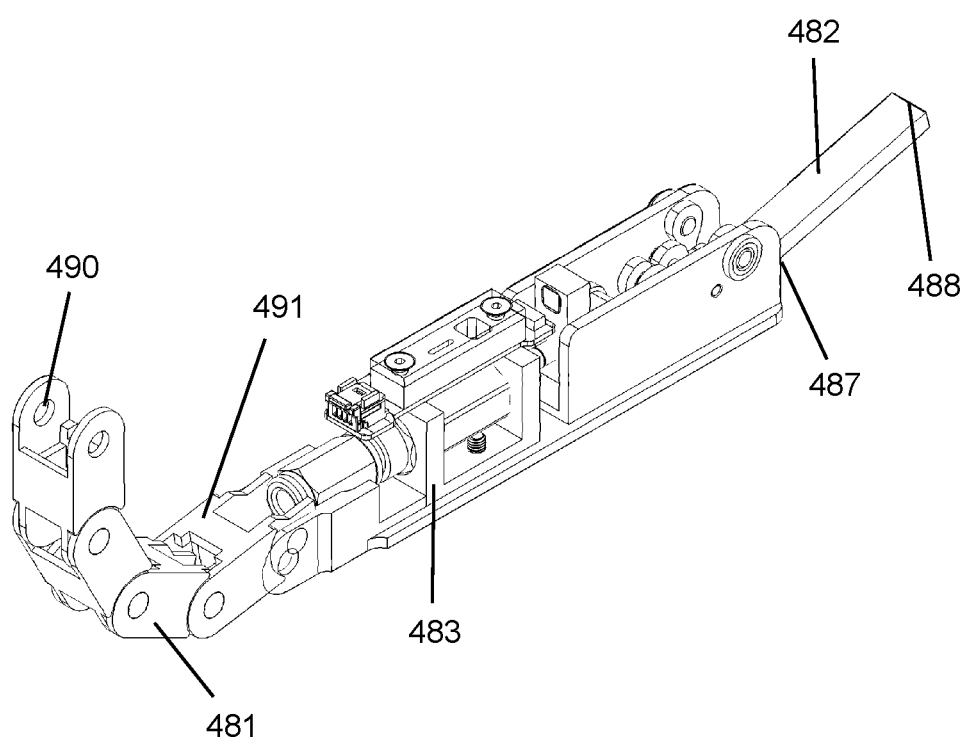

FIG. 11 illustrates an extendable member and flipper in accordance with an embodiment of the invention.

Figure 12:
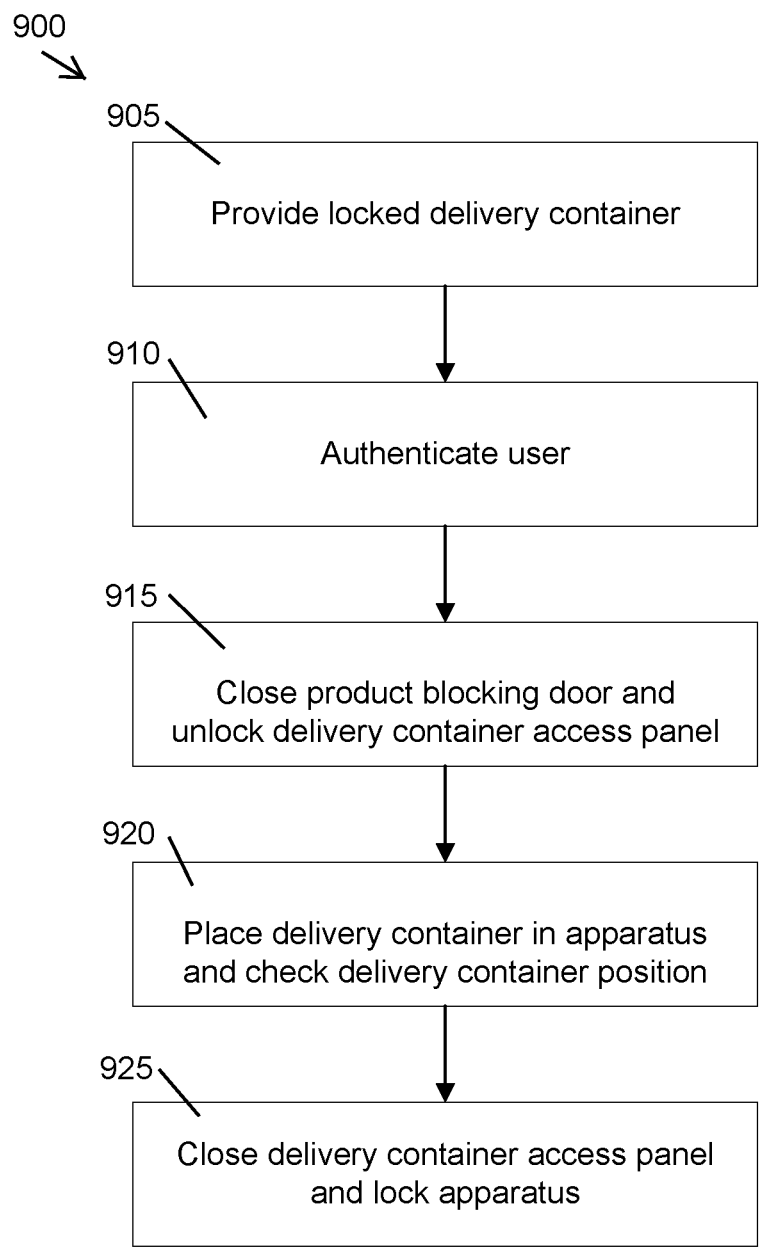

FIG. 12 illustrates a method for replacing a delivery container in accordance with an embodiment of the invention.

Figure 13:
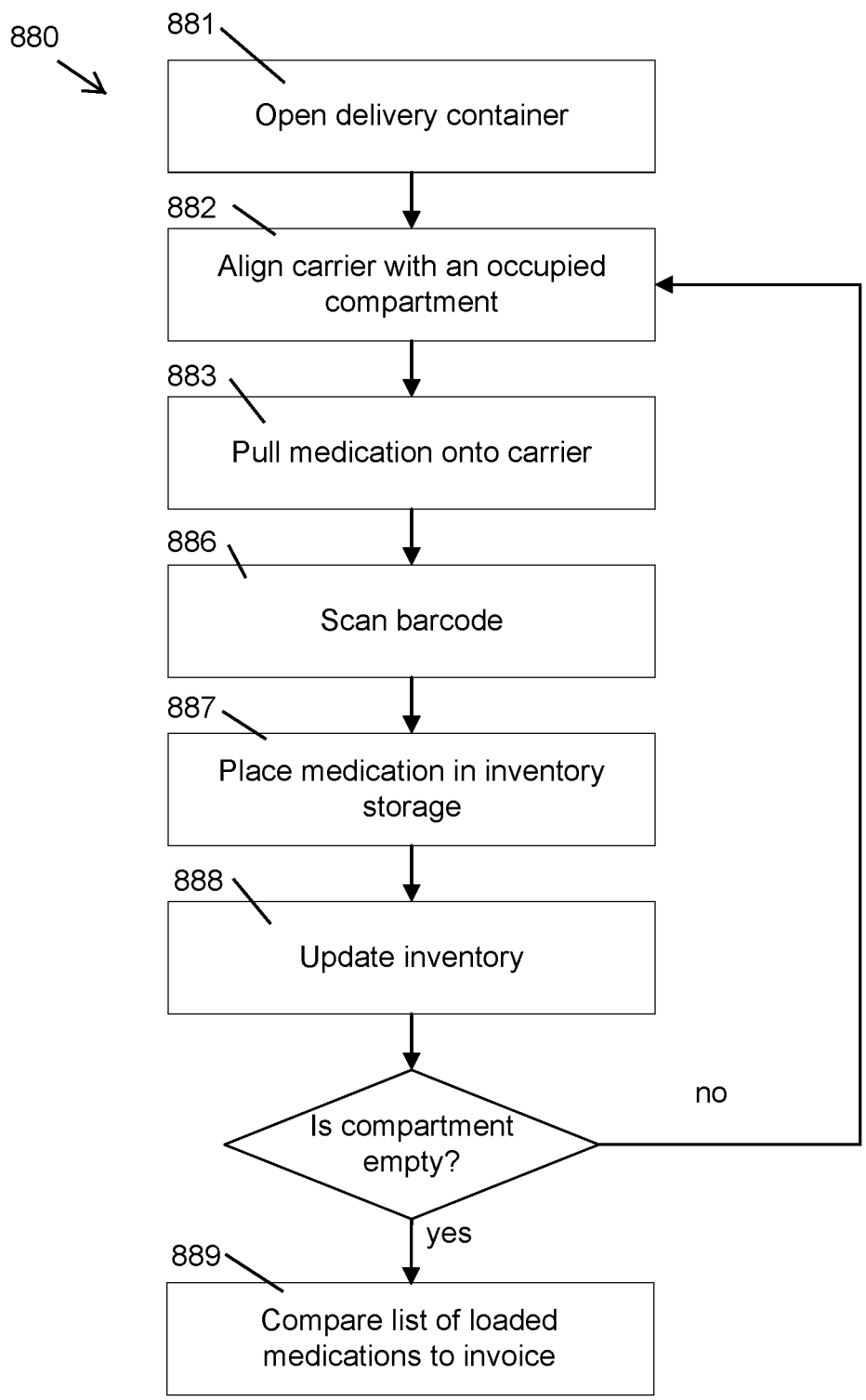

FIG. 13 illustrates a method for stocking an inventory storage container in accordance with an embodiment of the invention.

Figure 14:
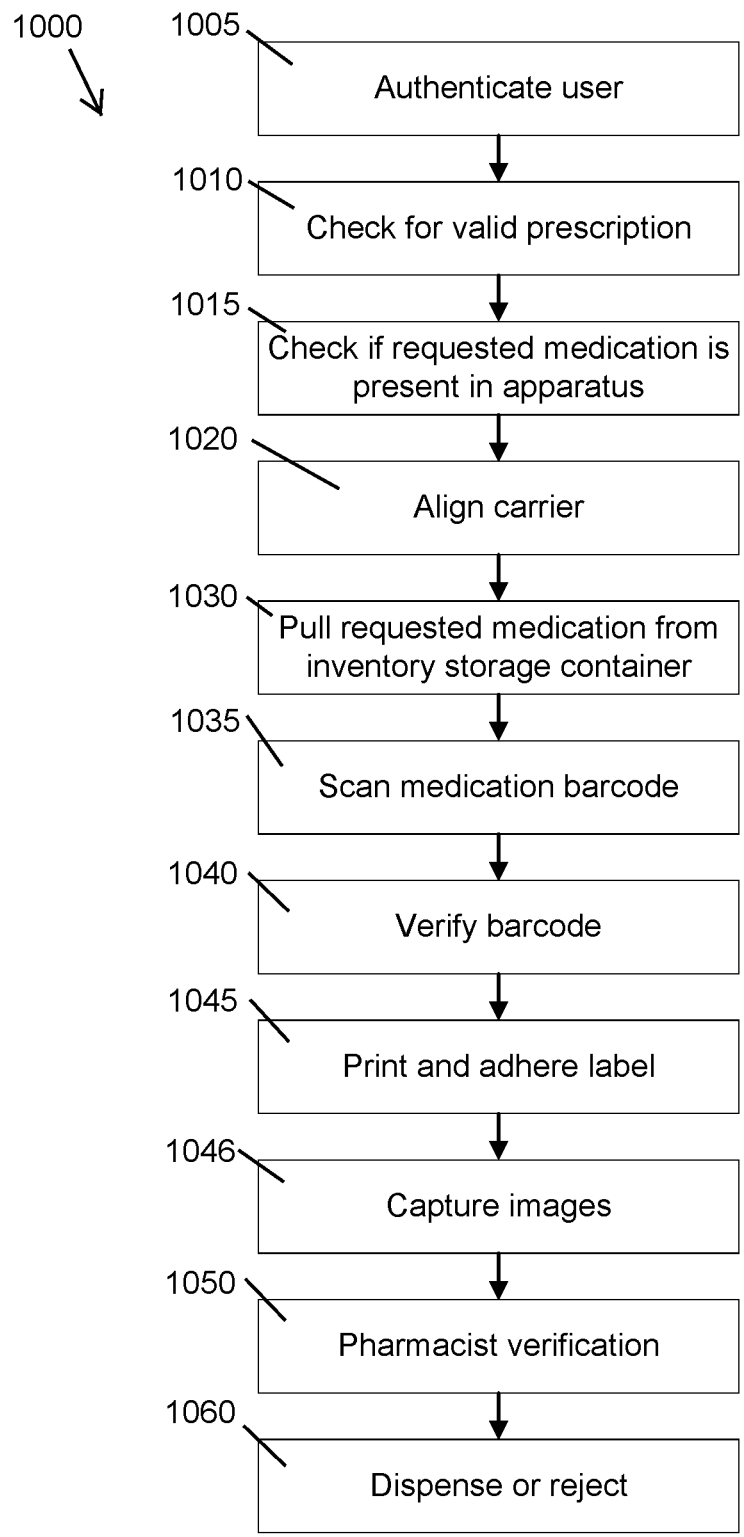

FIG. 14 illustrates a method for dispensing a medication in accordance with an embodiment of the invention.

Figure 15:
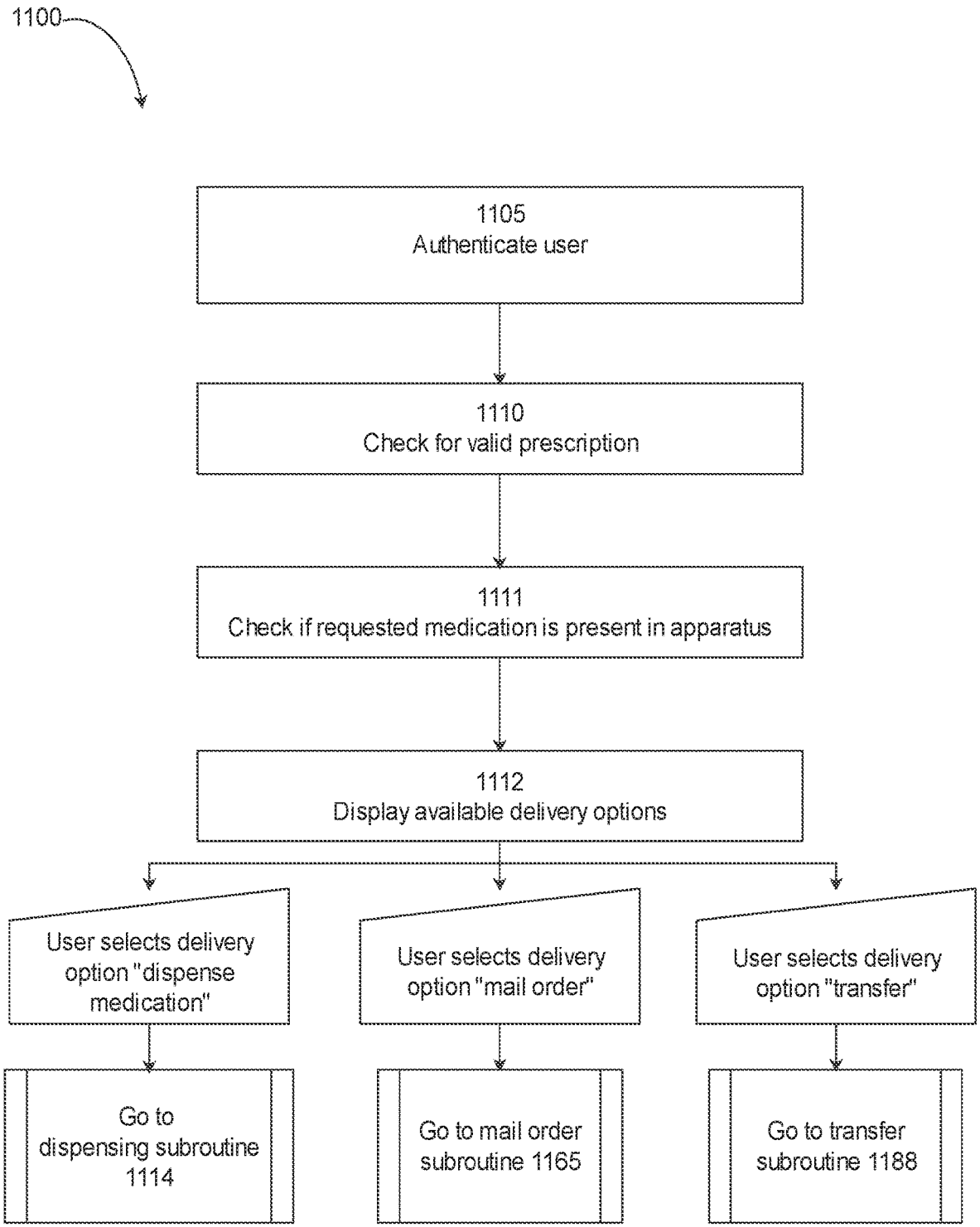

FIG. 15 illustrates a method for dispensing a medication in accordance with an embodiment of the invention.

Figure 16:
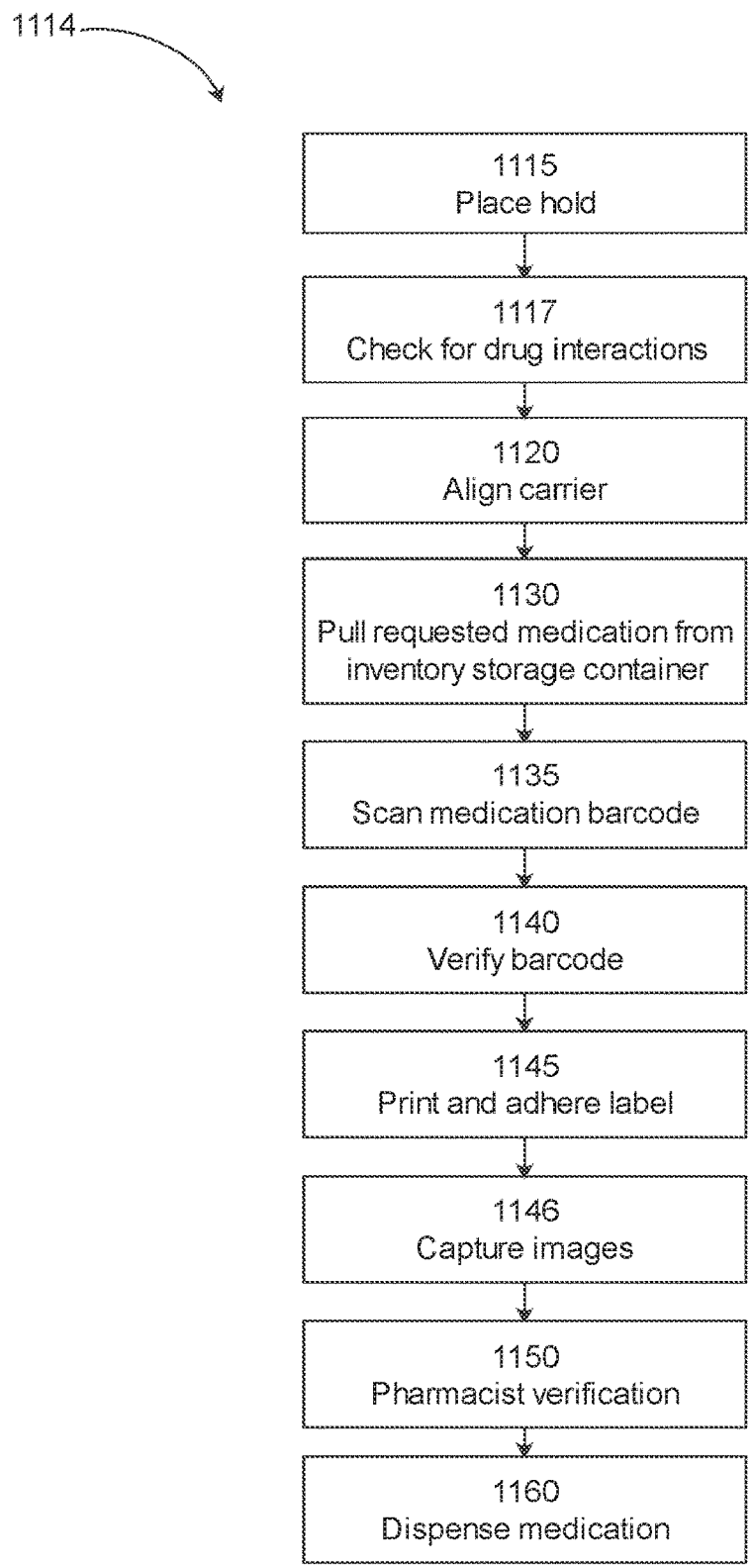

FIG. 16 illustrates a dispensing subroutine of a method for dispensing a medication in accordance with an embodiment of the invention.

Figure 17:
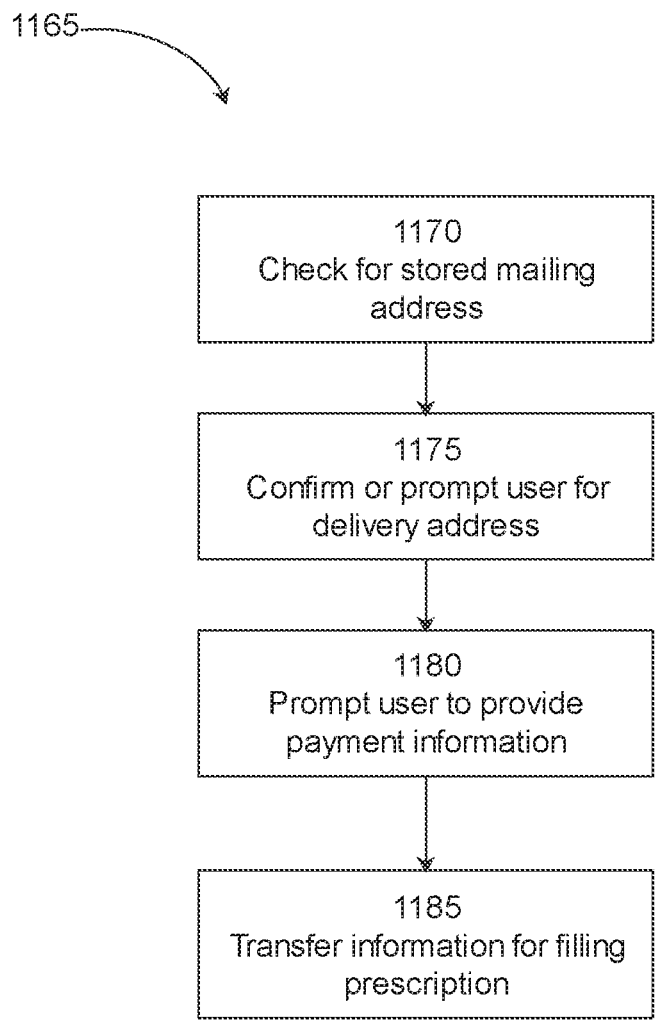

FIG. 17 illustrates a mail order subroutine of a method for dispensing a medication in accordance with an embodiment of the invention.

Figure 18:
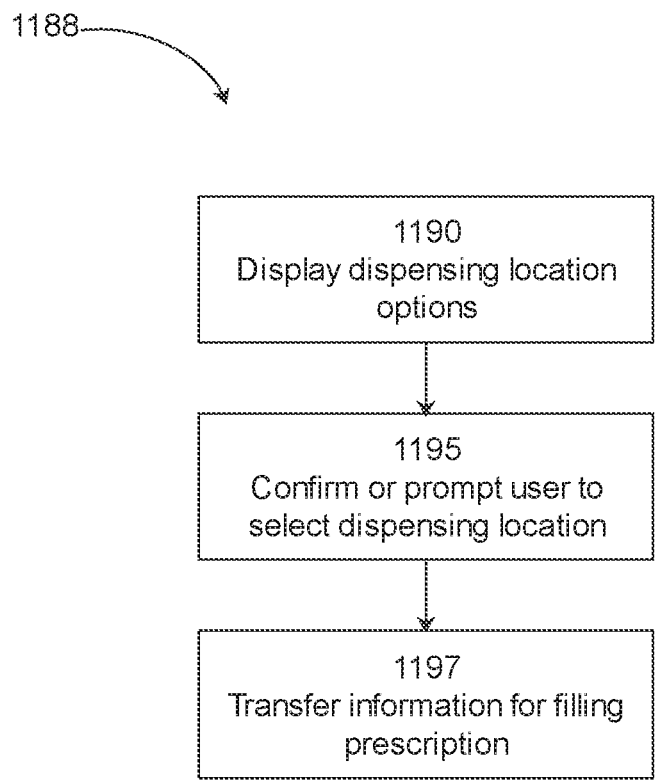

FIG. 18 illustrates a transfer subroutine of a method for dispensing a medication in accordance with an embodiment of the invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. Some components of the apparatus are not shown in one or more of the figures for clarity and to facilitate explanation of embodiments of the present invention.

Throughout the disclosure, the terms patient and user may be used interchangeably.

In accordance with one embodiment, FIG. 1, FIG. 2, FIG. 3, FIG. 4, and FIG. 5 illustrate an apparatus 1 for storing and dispensing medications. In one embodiment, apparatus 1 comprises a frame 10. Inventory storage 20 comprising one or more foam storage plates 225 for storing medications, stationary tracks 50 and 60, a printer assembly, a computer comprising a hardware processor, and an input device 100 are attached to frame 10.

An enclosure may attach to the frame 10 to completely surround the apparatus 1 and prevent access to the control electronics and other internal components of the apparatus 1 and items stored in the apparatus 1. In one embodiment, the enclosure comprises a plastic covering. In other embodiments, the enclosure may comprise a covering made from metal, wood, or another material capable of enclosing the internal components of the apparatus 1.

The temperature and humidity within the enclosure may be controlled to ensure that medications are stored under proper conditions. Temperature and humidity sensors read environmental conditions, and can activate heating or cooling systems as needed to regulate conditions within the enclosure. Cooling fans placed on various components of the apparatus 1 also assist in regulating the temperature within the apparatus 1.

A section of enclosure material may also be placed inside the apparatus 1 to cover electronics, preventing a technician with access to the internal components of apparatus 1 from accidentally touching the electronics.

Frame

Frame 10 defines a generally box-shaped structure capable of providing stable mounting points for other components of the apparatus 1. Frame 10 may comprise rails defining the corners of the box-shaped structure. Frame 10 may further comprise additional rails or cross bracing to provide stability or mounting points for components of the apparatus 1. Frame 10 may be constructed from metal, wood, plastic, or other rigid material capable of attaching to and supporting other structures and sub-systems of the apparatus 1. Wires connecting various parts of the apparatus may be routed through the frame 10 such that wiring is not exposed.

Casters may be attached to frame 10 to allow apparatus 1 to be moved from place to place. The casters may be lockable, preventing unexpected movement of the apparatus 1.

Carrier Assembly

In one embodiment, a carrier 400 is configured to retrieve items and move items between sub-systems of the apparatus 1. The carrier 400 can be moved horizontally and vertically, allowing the carrier 400 to access any compartment 226 of any foam storage plate 225 within the apparatus 1 or delivery container 700, or any other sub-system of the apparatus 1. The carrier 400 may comprise a mechanical hand, pincer device, suction device, platform, or other structure capable of picking and placing items stored in apparatus 1 and moving items between sub-systems of apparatus 1.

A stationary track 50 extends from a first rail of the frame 10 to the parallel rail of the frame 10 on the same side of the apparatus 1. Likewise, stationary track 60 extends from the same first rail of the frame 10 to the same parallel rail of the frame 10 on the same side of the apparatus 1. Stationary track 50 is situated near the top of the frame 10, stationary track 60 is situated near the bottom of the frame 10, and stationary tracks 50 and 60 are parallel to each other. Stationary tracks 50 and 60 are fixedly attached to the frame 10.

A moving carrier track 410 extends from stationary track 50 to stationary track 60. An upper end of the moving carrier track 410 may be connected to stationary track 50 by an upper carrier track carriage 420 that engages a channel in stationary track 50. Similarly, a lower end of the moving carrier track 410 may be connected to stationary track 60 by a lower carrier track carriage 430 that engages a channel in stationary track 60. A belt situated within the channel of stationary track 50 engages both the upper carrier track carriage 420 and the shaft of an upper carrier track motor 440. Another belt situated within the channel of stationary track 60 engages both the lower carrier track carriage 430 and the shaft of a lower carrier track motor 445. By rotating the shaft of the upper carrier track motor 440 and the lower carrier track motor 445, the moving carrier track 410 is moved horizontally. In one embodiment, a connecting rod attached to the shaft of either upper carrier track motor 440 or lower carrier track motor 445 extends between stationary tracks 50 and 60 and engages each belt situated within the channels of each of stationary tracks 50 and 60, allowing one motor to drive both of the belts responsible for the movement of the moving carrier track 410. By using one motor and a connecting rod in this manner, the speeds of and distances traveled by the upper carrier track carriage 420 and the lower carrier track carriage 430 are the same. Limit switches may be located at each end of stationary tracks 50 and 60 to indicate when the carrier track carriages 420 and 430 have reached the ends of their travel ranges.

A carrier carriage 460 engages a channel in the moving carrier track 410. A belt situated within the channel of the moving carrier track 410 engages the carrier carriage 460 and the shaft of a carrier carriage motor 470. By rotating the shaft of the carrier carriage motor 470, the carrier carriage 460 is moved vertically along the moving carrier track 410. Limit switches may be located at each end of the moving carrier track 410 to indicate when the carrier carriage 460 has reached the ends of its travel range.

The carrier 400 is mounted to the carrier carriage 460. As shown in FIG. 10, the carrier 400 comprises one or more container engaging surfaces 480 capable of engaging and holding a container. Multiple container engaging surfaces 480 may be positioned relative to each other in order to form an angle that prevents containers being held by the container engaging surfaces 480 from rolling off the carrier 400. Each container engaging surface 480 comprises one or more rollers 484, each roller 484 being generally parallel to other rollers 484 of that container engaging surface 480. One or more carrier roller belts 485 engage and surround the rollers 484 of a container engaging surface 480. A container being held on carrier 400 may be rotated by rotating the one or more rollers 484 of the one or more container engaging surfaces 480. As rollers 484 are rotated, the one or more belts 485 are moved; thus causing the container held on carrier 400 to rotate. Rotation of rollers 484 may be accomplished by a motor, servo, or other device capable of rotating the rollers 484.

As shown in FIG. 11, the carrier 400 further comprises an extendable member 481 configured to pass beneath container engaging surfaces 480, and to extend into and engage containers stored in a compartment 226 of foam storage plate 225. The extendable member 481 comprises a chain, cable, strip, or other material capable of being held rigid when extended and rolled into a coil when not extended. When extended, the extendable member 481 is capable of extending the full depth of the compartment 226.

A first end 490 of extendable member 481 is connected to the shaft of an extendable member motor 486. Extension of the extendable member 481 may be accomplished by rotating the shaft of the extendable member motor 486 in a first direction, causing the extendable member 481 to extend. Retraction of the extendable member 481 may be accomplished by rotating the shaft of the extendable member motor 486 in the opposite direction, causing the extendable member 481 to return to a coiled state. A tensioning mechanism may assist with the retraction of the extendable member 481 to prevent the extendable member 481 from binding up as it returns to its coiled state. A sensor may be provided to indicate when the extendable member 481 has been fully extended or retracted. Further, a coil containment compartment 489 disposed on the carrier 400 may surround the extendable member 481 while it is in its retracted and coiled state, causing the extendable member 481 to coil evenly on itself and prevent tangling of the extendable member 481.

Carrier 400 further comprises a flipper 482. Flipper 482 comprises a strip of rigid material having a first flipper end 487 and a second flipper end 488. First flipper end 487 is connected to a second end 491 of extendable member 481 via a flipper actuator 483, and the flipper 482 is capable of being rotated about the first flipper end 487.

To retrieve a container stored in a compartment 226 adjacent to the carrier 400, extendable member motor 486 is rotated in a first direction, causing extendable member 481 to uncoil and extend beneath the container engaging surfaces 480 and into the compartment channel associated with the compartment 226. When the first flipper end 487 has reached the end of the container in the compartment 226 that is furthest from the carrier 400, flipper 482 is actuated by the flipper actuator 483 to rotate about the first flipper end 487 in a first direction until flipper 482 forms an approximately 90 degree angle to extendable member 481. The extendable member motor 486 can then be rotated in a second direction, causing extendable member 481 to retract, and causing flipper 482 to engage a surface of the container in the compartment 226 that is furthest from the carrier 400, pulling the container toward the carrier 400. This motion of the extendable member 481 continues until a sensor indicates that a container is situated on the container engaging surfaces 480. At this point, flipper 482 is actuated to rotate about the first flipper end 487 in a second direction until flipper 482 is generally parallel to extendable member 481 and can pass beneath the container engaging surfaces 480.

To place a container being held on the carrier 400 into a compartment 226 adjacent to the carrier 400, extendable member motor 486 is rotated as needed to position second flipper end 488 near the end of the container on the carrier 400 that is furthest from the compartment 226. Flipper 482 is then actuated to rotate about the first flipper end 487 in a first direction until flipper 482 forms an approximately 90 degree angle to extendable member 481. The extendable member motor 486 can then be rotated in a first direction, causing extendable member 481 to extend beneath the container engaging surfaces 480, and causing flipper 482 to engage the surface of the container on the carrier 400 that is furthest from the compartment 226, pushing the container toward the compartment 226. This motion of the extendable member 481 continues until a sensor indicates that the flipper 482 has reached the edge of the compartment 226, indicating that the container has been positioned entirely in the compartment 226. At this point, the extendable member motor 486 is rotated in a second direction, causing the extendable member 481 to retract, until flipper 482 can rotate without interfering with containers in the compartment 226. Flipper 482 is then actuated to rotate about the first flipper end 487 in a second direction until flipper 482 is generally parallel to extendable member 481 and can pass beneath the container engaging surfaces 480.

Foam Storage Plates

As shown in FIGS. 2, 3, 4, and 6, inventory storage 20 comprises one or more foam storage plates 225 attached to the frame 10, providing a structure within the apparatus 1 where one or more medications may be stored. Each foam storage plate 225 comprises one or more compartments 226, wherein each compartment 226 is accessible to the carrier 400, and a medication bottle or box can be placed in each compartment 226. Foam storage plate 225 may accommodate round bottles, square bottles, boxes, or another container type. Each compartment 226 may comprise a generally cylindrical hole in the foam storage plate 225. Compartments 226 may vary in size to allow various sizes of medication packaging to be stored while maximizing the number of compartments 226; thus maximizing the number of medications that can be stored in a foam storage plate 225. Each compartment 226 may further comprise one or more flexible teeth 227. Teeth 227 may be small pieces of the foam storage plate 225 that engage the medication packaging. Teeth 227 may expand and compress to allow for various sizes of medication packaging to be stored in a compartment 226.

The use of foam storage plates 225 is advantageous because foam is an inexpensive and lightweight material. In addition, foam storage plates 225 are advantageous because medication packaging is held securely in the inventory storage container 20, preventing medications from falling out of the inventory storage container 20 due to vibration or tampering. Foam storage plates 225 may also be easily interchanged when damaged or when another size of compartment 226 is desired. In one embodiment, foam storage plates 225 clip into place without the use of tools. Placement of foam storage plates 225 against the enclosure of apparatus 1 provides further protection from medication packages falling out of the form storage plates 225.

Delivery Container

One embodiment of a delivery container 700 is shown in FIG. 7. The delivery container 700 provides a secure structure for introducing new medications into the apparatus 1. Delivery container 700 comprises a lockable delivery container enclosure 701 and one or more foam storage plates 225 disposed inside the enclosure 701. The foam storage plates used in the delivery container 700 may be the same as those used in inventory storage 20. The foam storage plates 225 of the delivery container 700 may contain round bottles, square bottles, boxes, or another container type. Once the delivery container 700 has been placed inside the apparatus 1, each compartment 226 in each storage plate 225 is accessible to the carrier 400. Storage plates 225 are interchangeable, and storage plates with differing sizes of compartments 226 may be placed inside the delivery container 700 to accommodate various sizes of medication packaging.

Printer Assembly

The printer assembly prints patient information, dosage instructions, QR code barcodes for accessing additional product information, and other information on an adhesive label, and adheres the label to medication packaging to prepare the medication for being dispensed to a patient. The printer assembly comprises a printer assembly mount 810, a label printer 800, and a label handling assembly 845. The printer assembly mount 810 provides an attachment point to the frame 10 and a support surface for other printer assembly components.

As shown in FIG. 9, the label handling assembly 845 comprises a rail 850 attached to the printer assembly mount 810. A labeler carriage 870 engages and is movable along the rail 850 in a direction that is generally parallel to the rail 850 in order to move printed labels from the label printer 800 to a container disposed on the carrier 400. In one embodiment a labeler 871 comprises a flat piece of metal, plastic, or other rigid material having a first end and a second, opposite, end. The first end of the labeler 871 is attached to the labeler carriage 870. The labeler 871 is capable of being rotated around an axis positioned at the first end of the labeler 871 such that the second end of the labeler 871 can be moved between raised and lowered positions. The labeler 871 further comprises a first side and a second, opposite, side with one or more openings passing from the first side to the second side. Mounted to the first side of the labeler 871 are one or more fans 872 configured to pull air through the one or more openings in the labeler 871 such that air moves from the second side to the first side.

In order to move a printed label from the label printer 800 to a container on the carrier 400, the labeler carriage 870 is moved along the rail 850 until the labeler 871 is generally aligned with the printed label on the label printer 800. The labeler 871 is rotated around its first end such that the labeler 871 is placed in its lowered position near the printed label on the label printer 800. The one or more fans 872 are powered, causing air to pass from the second side of the labeler 871 to the first side of the labeler 871; thus causing the non-adhesive side of the label to temporarily cling to the labeler 871. Labeler 871 is then rotated about its first end to its raised position, and the labeler 871 is moved along the rail 850 until the labeler 871 and printed label are generally aligned with the container being held on the carrier 400. The labeler 871 is then rotated around its first end such that the labeler 871 is placed in its lowered position, and the adhesive side of the label engages the container on the carrier 400. In one embodiment, the container on the carrier 400 is pressed into a wedge constructed of foam or similar flexible material, causing the label to fully adhere to the container. In another embodiment, the container on the carrier 400 may be rotated to wrap the label around the container; thus fully adhering the label to the container.

The label printer 800 is attached to the printer assembly mount 810, and is configured to print labels for placement on medication packaging dispensed by the apparatus 1. In one embodiment, the label printer 800 may comprise a commercially available label printer.

A dispensing chute 830 is positioned near the label handling assembly 845. Medication that has been labelled and approved for dispensing is placed into an opening of the dispensing chute 830, travels through the dispensing chute 830, and exits the dispensing chute 830 through a dispensing window 840 that is accessible from the outside of the apparatus 1. A pad made of foam, fabric, or other similar material may be placed at a lower end of dispensing chute 830 to avoid damaging medications and to reduce noise. Rejected medication may be directed through a rejection chute.

One or more barcode scanners for reading barcodes on medication packaging may be mounted near the label handling assembly 845. The barcode scanner may comprise a one-dimensional or a two-dimensional barcode scanner. As some medications are shipped with one-dimensional barcodes, and some with two-dimensional barcodes, both a one-dimensional barcode scanner and a two-dimensional scanner may be mounted near the label handling assembly 845 to accommodate a variety of barcode types. In addition, an internal camera and lighting for capturing images of the medication packaging may be mounted near the label handling assembly 845. Using barcode reading software, the barcode scanner may be implemented with a camera. An internal camera and lighting may also be mounted inside apparatus 1 for machine diagnostic purposes.

Computer and Centralized Database

A computer mounts to the frame 10, and controls the function of all sub-systems of the apparatus 1. The computer may communicate electronically with a centralized database that contains patient information, medication information, drug interaction information, and other data relevant to the dispensing of medications. Data storage components installed on the computer may store information regarding the types and locations of all medications stored in inventory storage 20. The types and locations of all medications stored in inventory storage 20 may also be communicated by the computer to the centralized database.

The computer may communicate with a centralized database that stores information for all installations of the apparatus 1. The centralized database may contain drug interaction information, client information, information regarding what medications are stored in each installation of the apparatus 1, and other data. The computer may communicate with the centralized database to obtain information stored in the centralized database and to upload information regarding transactions the apparatus 1 has engaged in.

Users (patients, doctors, pharmacists, etc.) may interact with the centralized database to determine where they can find an apparatus 1 that contains the medications they need. If a user needs multiple medications, then the user may be advised where the closest apparatus 1 having all of their medications is located. If there isn't an apparatus 1 that has everything the user needs, then the necessary medications can be ordered and stocked in an apparatus 1 in a location that is convenient for the user. Trends can be mined from dispensing information to predict an optimal inventory for a particular apparatus 1. As the optimal inventory changes or products expire, the old stock can be discarded via the rejection chute.

Each major sub-assembly of the apparatus 1 has a separate controller in communication with the computer, and the separate controllers are networked together.

In one embodiment, the computer comprises a commercially available personal computer.

Input Device

The input device 100 mounts to the frame 10, and allows users to interact with the apparatus 1. In one embodiment, the input device 100 comprises a touchscreen monitor. In other embodiments, the input device 100 may comprise a monitor, keyboard, mouse, magnetic strip reader, RFI reader, NFC reader, or other equipment capable of allowing a user to input and receive data from the apparatus 1. One or more external cameras may be installed on the apparatus 1. Such cameras may be configured to capture images of technicians and users interacting with the apparatus 1 and communicate the image capture data to the computer and to the centralized database.

Methods

As shown in FIG. 12, a method 900 for restocking medications in the apparatus 1 begins at step 905 with providing a locked delivery container 700 filled with medications. The delivery container 700 may be provided by a pharmaceutical manufacturer, pharmacist, or other supplier of medications. In one embodiment, the provider unlocks the delivery container 700, allowing the delivery container enclosure 701 to be opened and exposing compartments 226 of a foam storage plate 225 to be filled. After filling the delivery container 700, the provider locks the delivery container 700, and the filled and locked delivery container 700 can then be provided to a technician for placement in an apparatus 1.

The method continues at step 910 in which the technician opens the apparatus 1. Opening apparatus 1 may comprise logging into apparatus 1 by entering identifying information via the input device 100. The computer transmits the entered identifying information to the centralized database to verify if the technician is authorized to access the apparatus 1. If the computer determines from the centralized database that the technician is authorized to access the apparatus 1, then the computer actuates an access panel 5 lock to its open position at step 915 to allow the technician to open a delivery container access panel 5. Alternatively, the delivery container access panel 5 may be locked with a physical lock that is opened with a key. The key for opening delivery container access panel 5 may be different than keys used to unlock other access panels of apparatus 1 to restrict access to the various sections of apparatus 1 to those with authorization to access each section.

A product blocking door mounted near the access panel 5 blocks access to the inventory storage container 20 when the access panel 5 is open. Closure of the product blocking door creates two sections in the apparatus 1: the first section contains the inventory storage container 20 and most other internal components of apparatus 1, and the second section comprises a generally empty space for accommodating the delivery container 700. A sensor associated with the access panel 5 and connected to the computer senses whether the access panel 5 is open or closed. If software running on the computer determines that the delivery container access panel 5 is open, the carrier 400 is moved into the first section created by the product blocking door, and the product blocking door is then closed, preventing the technician from retrieving medications from the inventory storage container 20. When the delivery container access panel 5 is closed, the product blocking door may be opened to delivery container 700 unloading process to begin.

If the apparatus 1 contains an empty delivery container 700, the technician removes the empty delivery container 700 from the apparatus 1. The empty delivery container 700 may be returned to the supplier to be reused. At step 920, the technician places the filled and locked delivery container 700 in the apparatus 1. The technician then closes the delivery container access panel 5, and the computer actuates the delivery container access panel lock to its closed position at step 925.

The delivery container 700 replacement process is monitored by the computer. A sensor associated with the access door of the apparatus 1 and connected to the computer senses whether the access panel 5 is open or closed. If software running on the computer determines that the delivery container access panel 5 has been open longer than a predetermined amount of time allotted for a delivery container 700 replacement, an alert can be issued. In addition, an external camera may capture images of the technician performing the delivery container 700 replacement for security purposes.

A sensor mounted at the delivery container access panel 5 monitors placement of the delivery container 700. In one embodiment, the sensor comprises a light curtain surrounding the delivery container access panel 5. If the delivery container 700 has been loaded incorrectly, such as when the technician does not push the delivery container 700 all the way in, a sensor detects a disruption in the light produced by the light curtain. When an improperly placed delivery container 700 is detected, the process of unloading the delivery container 700 is delayed to avoid damage to medications, delivery container 700, and components of apparatus 1.

Immediately after a stocked delivery container 700 is placed in the apparatus 1, the computer and centralized database may not contain any information about what medications are stored in the delivery container 700. The identity of each medication is determined during a delivery container 700 unloading process that is initiated by software running on the computer after a stocked delivery container 700 has been placed in the apparatus 1. The delivery container 700 unloading process may proceed at night or during another period of inactivity.

Maintenance of the apparatus 1 proceeds in a similar manner to method 900, but instead of replacing the delivery container 700, the technician performs the prescribed maintenance after access is granted to internal components of the apparatus 1. The maintenance process is monitored by the computer. A sensor associated with an access door of the apparatus 1 and connected to the computer senses whether the access door is open or closed. If software running on computer determines that the access door has been open longer than a predetermined amount of time allotted for the prescribed maintenance, an alert can be issued. In addition, an external or external camera may capture images of the technician performing the maintenance for security purposes.

As shown in FIG. 13, a method 880 for unloading the delivery container 700 begins at step 881. After the computer determines that the apparatus 1 is closed (i.e., not being maintained or restocked), product blocking door is opened and the enclosure 701 of the delivery container 700 is opened at step 881.

To retrieve a medication container from a delivery container compartment 226, at step 882 the carrier 400 is positioned such that the carrier 400 is generally aligned with the compartment 226 to be unloaded.

At step 883, the medication container in the delivery container compartment 226 adjacent to the carrier is pulled out of the delivery container compartment 226 and onto the carrier 400.

At step 886, the barcode of the medication container on the carrier 400 is scanned by a barcode reader as the medication package is rotated on the carrier 400. The barcode reader communicates the barcode to the computer. Each medication sold has a unique barcode displayed on the medication packaging. Equipped with the barcode, the computer can query the central database to determine the type of medication, quantity of medication, the dimensions of the packaging, and other information associated with the unique barcode and stored in the central database. The computer identifies a compartment 226 in inventory storage 20 that can accommodate the newly added medication.

At step 887, the medication container being held on the carrier 400 is placed into a compartment 226 in inventory storage 20 chosen by the computer.

At step 888, the type and location within the inventory storage container 20 of the newly added medication is communicated to and stored in data storage components installed on the computer, and the type and location data may also be communicated and stored by the computer in the centralized database.

The method 880 proceeds by repeating steps 882, 883, 886, 887, and 888 until all medications have been removed from the compartment 226 in the delivery container 700 and placed in inventory storage 20.

Once all medications have been removed from the delivery container 700 and placed in the inventory storage container 20, the method 880 proceeds to step 889 in which a list of medications removed from the delivery container 700 during the unloading process is compared to an invoice listing all of the medications that were sent in the delivery container 700.

As shown in FIG. 14, a method 1000 for dispensing medications begins at step 1005 in which a user logs in to the apparatus 1 by entering identifying information via the input device 100. The computer transmits the entered identifying information to the centralized database to verify if the user is authorized to fill or refill prescriptions using the apparatus 1.

If the computer determines from information stored in the centralized database that the user is authorized to use apparatus 1, then the computer queries the centralized database to determine if the user has a valid prescription at step 1010. If the user has a valid prescription, the centralized database communicates the original prescription to the computer, and the method proceeds to step 1015 in which the computer queries the centralized database to determine if the requested medication is stored in the inventory storage container 20. Once a user selects to use a particular apparatus 1, a hold is placed on the requested medication at the centralized database. If the requested medication is not available from the apparatus 1, the unavailability is communicated to the user via the input device 100, and the transaction may be terminated. The computer may also query the centralized database to determine what other medications the user has filled to determine of any drug interactions that may occur if the patient takes the newly prescribed medication. If a drug interaction is determined, then a message indicating the drug interaction is communicated to the pharmacist for verification.

If the requested medication is available from the apparatus 1, then the method proceeds to step 1020 in which the carrier 400 is positioned such that the carrier 400 is generally aligned with the compartment 226 of inventory storage 20 where the requested medication is stored.

At step 1030, the medication container in the selected compartment 226 is pulled out of the compartment 226 and onto the carrier 400.

At step 1035, the barcode reader reads the barcode from the retrieved medication package as the medication is rotated on the carrier 400, and the barcode reader communicates the barcode to the computer. An image of the medication package may also be captured as the medication is rotated, and the image may be communicated to the computer.

At step 1040, the computer compares the barcode read by the barcode reader to the barcode that corresponds to the requested medication. If the barcode read by the barcode reader does not match the expected barcode that corresponds to the requested medication, the medication package is either placed back into a compartment 226 of inventory storage 20 or discarded through a discard chute, and steps 1015, 1020, 1030, 1035, and 1040 are repeated until the correct medication is retrieved or the computer indicates that the requested medication is not present in the apparatus 1.

If the barcode read by the barcode reader matches the expected barcode for the requested medication, the method proceeds to step 1045 in which the computer communicates instructions to the label printer 800 for printing a label containing patient information such as the patient's name and dosage instructions. A QR code may also be included on the label to enable the user to obtain more information using software running on their personal cell phone or other device. The printed label extends from the label printer 800. In order to move the printed label from the label printer 800 to the container on the carrier 400, the labeler carriage 870 is moved along the rail 850 until the labeler 871 is generally aligned with the printed label on the label printer 800. The labeler 871 is rotated around its first end such that the labeler 871 is placed in its lowered position near the printed label on the label printer 800. The one or more fans 872 are powered, causing air to pass from the second side of the labeler 871 to the first side of the labeler 871; thus causing the non-adhesive side of the label to temporarily cling to the labeler 871. Labeler 871 is then rotated about its first end to its raised position, and the labeler 871 is moved along the rail until the labeler 871 and printed label are generally aligned with the container being held on the carrier 400. The labeler 871 is then rotated around its first end such that the labeler 871 is placed in its lowered position, and the adhesive side of the label engages the container on the carrier 400. In one embodiment, the container on the carrier 400 is pressed into a wedge constructed of foam or similar flexible material, causing the label to fully adhere to the container. In another embodiment, the container on the carrier 400 may be rotated to wrap the label around the container; thus fully adhering the label to the container.

At step 1046, one or more images of the medication packaging may be captured by the camera as the medication packaging is rotated on the carrier 400. In one embodiment, an image of the medication packaging is captured both before and after the label is adhered to the medication packaging. The captured images may be communicated to the computer and to the centralized database.

At step 1050, the computer communicates the original prescription, the image of the unlabeled medication packaging, and the image of the labeled packaging to the centralized database. The centralized database notifies the pharmacist that there is a prescription that needs to be verified. The pharmacist views the original prescription and the images pertaining to the pending prescription, and approves or rejects dispensing of the medication based on a visual inspection of the medication. Prior to approving release of the container of medication to the user, the pharmacist verifies that the container contains the correct product by viewing the images of the labeled and unlabeled medication container and comparing one or more of the name of the medication, the National Drug Code (NDC) for the medication, the label that has been applied to the container of medication, the prescription, or any other information available in the images. The pharmacist also verifies that the dosage, frequency, and other patient instructions are correctly printed on the label that has been applied to the container of medication and determines if any harmful drug interactions may occur. If the pharmacist rejects dispensing the medication, then a message is displayed to the user via input device 100, and the rejected medication may be placed back into a compartment 226 of inventory storage 20 or discarded through the rejection chute. If the pharmacist approves dispensing the medication, the user is prompted via the input device 100 to enter payment information using a magnetic strip reader, chip reader, or other payment input means, and the method proceeds to step 1060 in which the medication is placed in the dispensing chute 830, and the user may access the dispensed medication through the dispensing window 840. In another embodiment, the dispensed medication may be placed in a locked holding area in the apparatus 1 and made available to the user following further authentication. If a dispensed medication will not be available immediately, the input device 100 may display status information such as ready, pending, an estimate of how much time remains before the dispensed medication will be available, or another status indicator and may request a phone number for the purpose of sending a text message to the user when the dispensed medication is ready to pick up.

To facilitate use of the apparatus 1 to dispense a prescription, in one embodiment a recorded message may play on the input device 100 to encourage users to touch the touch-screen or otherwise begin interacting with the apparatus 1. The recorded message may feature an image of a welcoming character to put the user at ease with using the apparatus 1, and in one embodiment the appearance of the character may change depending on the language option that the user chooses. In another embodiment, the character that appears may be an image of the user's doctor. The message may provide step-by-step instructions to guide the user through using the apparatus 1 to dispense a medication. The use of a recorded message and welcoming image is intended to make the user comfortable with using the apparatus 1, and is advantageous because it may prevent the user from calling a pharmacist to complete the transaction.

Instructions for calling a pharmacist for a consultation may be provided via the input device 100. In one embodiment, the user may be instructed of a phone number to call via the input device 100. In another embodiment, the user may provide a phone number for a pharmacist to call for a consultation.

Data stored in the centralized database may be used to recognize trends in dispensing data, and to anticipate what types of medications may be required in a particular apparatus. For example, trend data may indicate when flu medications should be distributed to installations of the apparatus 1 in advance of flu season. To facilitate medications that are refilled regularly, the apparatus 1 may be pre-stocked to ensure that the refill medications are available when the user is likely to refill the prescription. Centralized storage of data also provides for the ability to provide data to users using remote software, for example an application running on a cell phone or similar device. The remote software may allow a user to identify the installation of the apparatus 1 nearest to their geographic location that contains all medications the user requires.

By coordinating through the centralized database, it is possible to use web-based and application based programs to locate the best apparatus 1 from a user's current location and to place a hold on a medication, provide payment, etc. For example, the application may rank apparatus 1 locations based on proximity to the user, availability of requested medications, or other user-specified criteria. To limit the space consumed by on-hold prepaid items, either through normal interaction or web interface, a technician can move the product from the apparatus 1 to a lock box. Access to the lock box is controlled by the apparatus 1.

As shown in FIG. 15, a method 1100 for dispensing medications begins at step 1105 in which a user logs in to the apparatus 1 by entering or supplying identifying information via the input device 100. Supplying identifying information may take the form of scanning a government issued identification or another form of identification. Alternatively, identifying information may be manually entered, for example by entering a username and password associated with an account associated with the user. The computer transmits the entered identifying information to the centralized database to verify if the user is authorized to fill or refill prescriptions using the apparatus 1.

After the computer or hardware processor of apparatus 1 authenticates the user at step 1105, the computer queries the centralized database to determine if the user has a valid prescription at step 1110. Alternatively, the computer may prompt the user to input a prescription via an input device 100. For example, the user may input a paper prescription that is imaged by a camera of the apparatus 1. If the user has a valid prescription, the centralized database communicates the original prescription to the computer, and the method proceeds to step 1111 in which the computer queries the centralized database to determine if the requested medication is stored in the inventory storage container 20 of the apparatus 1. The method then proceeds to step 1112 in which the computer displays delivery options to the user via the input device 100 and requests that the user select a delivery option. The delivery options include receiving the medication from the apparatus 1, placing a mail order for medications or requesting delivery of medications, and transferring the prescription to another pharmacy or other dispensing location such as another apparatus 1. Only delivery options that are possible to complete may be displayed to the user on the input device 100. For example, if the medication is not available from the apparatus 1, then the option of receiving the medication at the apparatus 1 may be omitted from the list of delivery options displayed to the user, and the user is prompted to select placing a mail order or having the medications delivered, transferring to another pharmacy or another dispensing location (such as another apparatus 1), or cancelling the transaction. If the medication is unavailable at the apparatus 1 but is available at another apparatus 1, then the location of the other apparatus 1 may be communicated as a delivery option, and the user may be given the option of transferring the medication to the other apparatus 1 where the medication is available. If a particular delivery option is unavailable, a message communicating why the option is not provided may be displayed on input device 100, and the remaining delivery options as well as an option to cancel the transaction may be displayed. In addition to the delivery options, the apparatus 1 may display pricing information, travel distance information, and/or timing information for each available delivery option, allowing the user to thoroughly evaluate the advantages or disadvantages of each delivery option and make an informed choice when choosing where to fill his or her prescription. Pricing information may include the cost of filling the prescription at the apparatus 1, the prices of the medication(s) through various available mail order or delivery options, the prices of the medication(s) at nearby pharmacies, or other relevant pricing information such as a comparison of name brand vs. generic versions of the medication(s). Travel distance information may include the distance to nearby pharmacies or other dispensing locations. Timing information may include an estimated wait time if filling the prescription at the apparatus 1, the estimated wait time if the patient chooses mail order or delivery, and the estimated wait time for nearby pharmacies or other dispensing locations. By providing pricing, travel distance, and/or timing information, patients can consider the advantages and disadvantages of each delivery option and are given a complete choice in choosing where to fill their prescriptions. As example of this consideration: mail order might be cheaper but the patient will have to wait to receive the medication(s); dispensing at the apparatus 1 may be more expensive, but the patient can conveniently receive the medication(s) immediately; the patient can see that The Pharmacy on 5th Street is $X and 5 miles away but the Grocery Pharmacy on 6th is $Y and 10 miles away. In each example, the patient can consider the factors of price, distance, time, and convenience in making a decision that is right for the patient under the circumstances. In addition, the choice can be made early in the dispensing process before the patient has communicated with a pharmacist, making it easy for the patient to choose the best delivery option without feeling obligated to complete a transaction in progress. Once the user has selected a delivery option via the input device 100, the method proceeds to the appropriate subroutine.

Subroutine for Dispensing the Medication from the Apparatus

If the user selects at step 1112 the delivery option of receiving the medication at the apparatus 1, then them method proceeds the dispensing subroutine 1114. As shown in FIG. 16, the dispensing subroutine 1114 begins at step 1115 in which a hold is placed on the requested medication at the centralized database. At step 1117 the computer may also query the centralized database to determine what other medications the user has filled to determine any drug interactions that may occur if the patient takes the newly prescribed medication. If a drug interaction is determined, then a message indicating the drug interaction is communicated to the pharmacist for verification.

If the requested medication is available from the apparatus 1, then the method proceeds to step 1120 in which the carrier 400 is positioned such that the carrier 400 is generally aligned with the compartment 226 of inventory storage 20 where the requested medication is stored.

At step 1130, the medication container in the selected compartment 226 is pulled or retrieved from the compartment 226 by the carrier 400.

At step 1135, the barcode reader reads the barcode from the retrieved medication package as the medication is rotated on the carrier 400, and the barcode reader communicates the barcode to the computer. An image of the medication package may also be captured as the medication is rotated, and the image may be communicated to the computer.

At step 1140, the computer compares the barcode read by the barcode reader to the barcode that corresponds to the requested medication. If the barcode read by the barcode reader does not match the expected barcode that corresponds to the requested medication, the medication package is either placed back into a compartment 226 of inventory storage 20 or discarded through a discard chute, and steps 1115, 1120, 1130, 1135, and 1140 are repeated until the correct medication is retrieved or the computer indicates that the requested medication is not present in the apparatus 1.

If the barcode read by the barcode reader matches the expected barcode for the requested medication, the method proceeds to step 1145 in which the computer communicates instructions to the label printer 800 for printing a label containing patient information such as the patient's name and dosage instructions. A QR code may also be included on the label to enable the user to obtain more information using software running on their personal cell phone or other device. The printed label extends from the label printer 800. In order to move the printed label from the label printer 800 to the container on the carrier 400, the labeler carriage 870 is moved along the rail 850 until the labeler 871 is generally aligned with the printed label on the label printer 800. The labeler 871 is rotated around its first end such that the labeler 871 is placed in its lowered position near the printed label on the label printer 800. The one or more fans 872 are powered, causing air to pass from the second side of the labeler 871 to the first side of the labeler 871; thus causing the non-adhesive side of the label to temporarily cling to the labeler 871. Labeler 871 is then rotated about its first end to its raised position, and the labeler 871 is moved along the rail until the labeler 871 and printed label are generally aligned with the container being held on the carrier 400. The labeler 871 is then rotated around its first end such that the labeler 871 is placed in its lowered position, and the adhesive side of the label engages the container on the carrier 400. In one embodiment, the container on the carrier 400 is pressed into a wedge constructed of foam or similar flexible material, causing the label to fully adhere to the container. In another embodiment, the container on the carrier 400 may be rotated to wrap the label around the container; thus fully adhering the label to the container.

At step 1146, one or more images of the medication packaging may be captured by the camera as the medication packaging is rotated on the carrier 400. In one embodiment, an image of the medication packaging is captured both before and after the label is adhered to the medication packaging. The captured images may be communicated to the computer and to the centralized database.

At step 1150, the computer communicates the original prescription, the image of the unlabeled medication packaging, and the image of the labeled packaging to the centralized database for pharmacist verification. The centralized database notifies the pharmacist that there is a prescription that needs to be verified. The pharmacist views the original prescription and the images pertaining to the pending prescription, and approves or rejects dispensing of the medication based on a visual inspection of the medication. Prior to approving release of the container of medication to the user, the pharmacist verifies that the container contains the correct product by viewing or performing a visual inspection of the images of the labeled and unlabeled medication container and comparing one or more of the name of the medication, the National Drug Code (NDC) for the medication, the label that has been applied to the container of medication, the prescription, or any other information available in the images. The pharmacist also verifies that the dosage, frequency, and other patient instructions are correctly printed on the label that has been applied to the container of medication and determines if any harmful drug interactions may occur. If the pharmacist rejects dispensing the medication, then a message is displayed to the user via input device 100, and the rejected medication may be placed back into a compartment 226 of inventory storage 20 or discarded through the rejection chute. If the pharmacist approves dispensing the medication, the user is prompted via the input device 100 to enter payment information using a magnetic strip reader, chip reader, or other payment input means. The user may also be prompted to provide insurance information at this time. During any part of the approval process of step 1150, the user or pharmacist may initiate communication between the user and pharmacist to discuss questions or otherwise facilitate the dispensing process. To initiate communicate, the hardware processor or computer establishes real-time communication over a communications network via an input device 100. The dispensing process may also include receiving a signature from the user. Release of the medication may be dependent on receiving a signature from the user.

The method then proceeds to step 1160 in which the medication is placed in the dispensing chute 830, and the user may access the dispensed medication through the dispensing window 840. Dispensing window 840 may comprise a door that can be switched between a locked state and an unlocked state. Once the dispensed medication is placed in the dispensing chute 830, the dispensing window 840 may be switched to an unlocked state for a period of time to allow the user to retrieve the dispensed medication. In another embodiment, the dispensed medication may be placed in a locked holding area in the apparatus 1 and made available to the user following further authentication. If a dispensed medication will not be available immediately, the input device 100 may display status information such as ready, pending, an estimate of how much time remains before the dispensed medication will be available, or another status indicator, and may request a phone number for the purpose of sending a text message to the user when the dispensed medication is ready to pick up.

Subroutine for Placing a Mail Order or Requesting Delivery of the Medication

If the user selects at step 1112 the delivery option of placing a mail order or requesting delivery of the medication, then the method proceeds to the mail order subroutine 1165. As shown in FIG. 17, the mail order subroutine 1165 begins at step 1170 in which the computer queries the centralized database to determine if the user has a physical mailing address stored in the centralized database. If the centralized database contains a physical mailing address for the user, the address is displayed using the input device 100. If no address is found for the user in the centralized database, then the computer displays to the user on input device 100 that there is no address on file for the user.

At step 1175, the computer requests address confirmation or entry from the user via input device 100. If an address was found at step 1170, then the user is asked to confirm delivery to the displayed address or enter a different address for delivery of the medication. If no address was found at step 1170, then the user is asked to enter an address for delivery of the medication. The computer may validate that the entered address is valid before proceeding. If the computer determines that the entered address is invalid, the user may be given the options of correcting the address, entering an alternative address, or proceeding with the address as entered.

At step 1180, the user is prompted via the input device 100 to enter payment information using a magnetic strip reader, chip reader, or other payment input means. The user may also be prompted to provide insurance information at this time.

The method then proceeds to step 1185 in which the prescription, address, payment information, and insurance information are forwarded to a participating pharmacy or other provider that is authorized to fill the prescription and ship it to the address provided by the user at steps 1170 and 1175. An approximate delivery date may be displayed on the input device 100. The user may be prompted for an email address and/or phone number for receiving shipping and delivery updates via email, phone, text message, or similar means.

Subroutine for Transferring the Prescription to a Pharmacy or Another Dispensing Location The delivery option of transferring the prescription includes transferring the prescription to a pharmacy or transferring the prescription to another apparatus 1. The option of transferring to another apparatus 1 is useful if the current apparatus 1 that the user is using does not have the required medication available. For purposes of this disclosure, transferring the prescription to a pharmacy may include transferring the prescription to another apparatus 1, a different type of medication dispensing kiosk, or another location where prescriptions are dispensed.

If the user selects at step 1112 the delivery option of transferring the prescription to another pharmacy or other dispensing location, then the method proceeds to the transfer subroutine 1188. As shown in FIG. 18, the transfer subroutine 1188 begins at step 1190 in which the computer queries the centralized database to determine if the user has a preferred pharmacy stored in the centralized database. If the centralized database contains a preferred pharmacy for the user, the address is displayed using the input device 100. If no preferred pharmacy is found for the user in the centralized database, then the computer displays a list of nearby pharmacies to the user on input device 100. Location information including physical address and/or distance from the current location may be provided to the user via the input device 100, allowing the user to choose a pharmacy or another apparatus 1 that is convenient for the user to visit. Pricing information for each pharmacy may be provided to the user via the input device 100, allowing the user to choose the lowest cost option for filling the prescription. Additional information may also be provided to the user about each pharmacy such as ratings, reviews, whether the building is ADA compliant, whether the building has a drive-through window, or whether the pharmacy accepts particular insurance plans.

At step 1195, the computer requests that the user select a pharmacy or other dispensing location. If a preferred pharmacy was found at step 1190, then the user may confirm transfer to the preferred pharmacy via the input device 100 or initiate selection of a different pharmacy or dispensing location. To select a different pharmacy, the user may choose from a list of nearby pharmacies, enter a zip code to search for pharmacies within a given radius of the entered zip code, or search for a pharmacy name or address. If no preferred pharmacy was found at step 1190, then the user may choose from the provided list of nearby pharmacies, enter a zip code to search for pharmacies within a given radius of the entered zip code, or search for a pharmacy name or address. At any point when a listing of pharmacies is provided, additional information may also be provided to the user about each pharmacy such as ratings, reviews, whether the building is ADA compliant, whether the building has a drive-through window, or whether the pharmacy accepts particular insurance plans.

Once the user has selected a pharmacy or other dispensing location at step 1195, the prescription is transferred to the selected pharmacy at step 1197. Payment or insurance information may be collected at apparatus 1 using a magnetic strip reader, chip reader, or other payment input means, in which case the payment or insurance information will be transferred to the selected pharmacy with the prescription. Alternatively, payment and insurance information may be collected at the pharmacy using traditional methods. An approximate time at which the prescription will be ready at the selected pharmacy may be displayed on the input device 100. The user may be prompted for an email address and/or phone number for receiving updates, questions, or other messages from the pharmacy via email, phone, text message, or similar means.

Regardless of the delivery method chosen, at any point the user may select an option to cancel the selected delivery method and return to step 1112 to choose a different delivery method.

To facilitate use of the apparatus 1 to dispense a prescription, in one embodiment a recorded message may play on the input device 100 to encourage users to touch the touchscreen or otherwise begin interacting with the apparatus 1. The recorded message may feature an image of a welcoming character to put the user at ease with using the apparatus 1, and in one embodiment the appearance of the character may change depending on the language option that the user chooses. In another embodiment, the character that appears may be an image of the user's doctor. The message may provide step-by-step instructions to guide the user through using the apparatus 1 to dispense a medication. The use of a recorded message and welcoming image is intended to make the user comfortable with using the apparatus 1, and is advantageous because it may prevent the user from calling a pharmacist to complete the transaction.

Instructions for calling a pharmacist for a consultation may be provided via the input device 100. In one embodiment, the user may be instructed of a phone number to call via the input device 100. In another embodiment, the user may provide a phone number for a pharmacist to call for a consultation.

Data stored in the centralized database may be used to recognize trends in dispensing data, and to anticipate what types of medications may be required in a particular apparatus. For example, trend data may indicate when flu medications should be distributed to installations of the apparatus 1 in advance of flu season. To facilitate medications that are refilled regularly, the apparatus 1 may be pre-stocked to ensure that the refill medications are available when the user is likely to refill the prescription. Centralized storage of data also provides for the ability to provide data to users using remote software, for example an application running on a cell phone or similar device. The remote software may allow a user to identify the installation of the apparatus 1 nearest to their geographic location that contains all medications the user requires.

By coordinating through the centralized database, it is possible to use web-based and application based programs to locate the best apparatus 1 from a user's current location and to place a hold on a medication, provide payment, etc. For example, the application may rank apparatus 1 locations based on proximity to the user, availability of requested medications, or other user-specified criteria. To limit the space consumed by on-hold prepaid items, either through normal interaction or web interface, a technician can move the product from the apparatus 1 to a lock box. Access to the lock box is controlled by the apparatus 1.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for dispensing one or more medications to a patient, the method comprising using at least one hardware processor of a medication-dispensing machine to:
   receive a prescription and an identification of the patient;
   querying inventory information stored in a centralized database to determine if the medication is present in an inventory storage component of the medication-dispensing machine;
   display to the patient using an input device of the medication-dispensing machine delivery options that are possible to complete using the medication-dispensing machine, wherein the delivery options comprise placing an order for the medication using the medication-dispensing machine, transferring the prescription using the medication-dispensing machine, and if the medication is present in the inventory storage component dispensing the medication at the medication-dispensing machine;
   receive an input indicating a delivery option selected by the patient; and
   complete the selected delivery option.

2. The method of claim 1 wherein the selected delivery option comprises dispensing the medication at the medication-dispensing machine, and dispensing the medication at the medication-dispensing machine comprises: retrieving a container of the identified medication from a plurality of containers of medication that are stocked within the medication-dispensing machine, wherein each of the plurality of containers of medication comprises a first barcode; scanning the first barcode of the retrieved container; generating a patient label based on at least the patient information; applying the patient label to the retrieved container; capturing an image of the labelled container, wherein the captured image shows the retrieved container and the patient label; providing the captured image and the electronic prescription over at least one network to a remote pharmacist; receiving approval over the at least one network from the remote pharmacist based on at least a visual inspection of the captured image and the electronic prescription by the remote pharmacist; wherein the visual inspection comprises matching the retrieved container, the patient information on the patient label, and the electronic prescription, and, based on the approval, releasing the labelled container to the patient.

3. The method of claim 2, wherein the medication-dispensing machine comprises a display, and wherein dispensing the medication at the medication-dispensing machine further comprises using the at least one hardware processor to establish real-time communication, over the at least one network, between the patient and the pharmacist via the display.

4. The method of claim 2, wherein the medication-dispensing machine comprises a dispensing enclosure with a door that can be switched between a locked state and an unlocked state, and wherein releasing the retrieved container to the patient comprises switching the door to an unlocked state.

5. The method of claim 2, wherein dispensing the medication at the medication-dispensing machine further comprises using the at least one hardware processor to receive a signature from the patient, and wherein releasing the retrieved container to the patient is further based on receiving the signature from the patient.

6. The method of claim 2, wherein dispensing the medication at the medication-dispensing machine further comprises using the at least one hardware processor to receive a payment for the medication from the patient, and wherein releasing the retrieved container to the patient is further based on the payment.

7. The method of claim 1 wherein the selected delivery option comprises ordering the medication, and ordering the medication comprises: prompting the patient for a delivery address; receiving an input indicating the delivery address; prompting the patient for payment information; receiving an input comprising payment information; and transferring information for filling the prescription.

8. The method of claim 7 wherein transferring information for filling the prescription comprises transferring the prescription and identification of the patient to a dispensing location that will fill and ship the prescription to the delivery address.

9. The method of claim 1 wherein the selected delivery option comprises transferring the prescription, and transferring the prescription comprises: displaying one or more dispensing location options; receiving an input comprising a selected dispensing location; and transferring information for filling the prescription to the selected dispensing location.

10. The method of claim 9 wherein transferring information for filling the prescription to the selected dispensing location comprises transferring the prescription and identification of the patient to a second medication dispensing-machine.

11. The method of claim 9 wherein transferring information for filling the prescription to the selected dispensing location comprises transferring the prescription and identification of the patient a pharmacy.

12. The method of claim 1 further comprising displaying pricing information, travel distance information, and timing information for each available delivery option.

* * * * *